US008361478B2

(12) United States Patent
Pau et al.

(10) Patent No.: US 8,361,478 B2
(45) Date of Patent: *Jan. 29, 2013

(54) RECOMBINANT VIRAL-BASED MALARIA VACCINES

(75) Inventors: Maria G. Pau, Leiden (NL); Lennart Holterman, Zoetermeer (NL); Jorn Kaspers, Leiden (NL); Antonius J. H. Stegmann, Katwijk (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/373,224

(22) Filed: Nov. 8, 2011

(65) Prior Publication Data

US 2012/0082694 A1 Apr. 5, 2012

Related U.S. Application Data

(60) Division of application No. 12/928,044, filed on Dec. 1, 2010, now Pat. No. 8,097,453, which is a continuation-in-part of application No. 11/975,396, filed on Oct. 18, 2007, now Pat. No. 7,867,764, which is a division of application No. 11/607,366, filed on Dec. 1, 2006, now Pat. No. 7,387,894, which is a division of application No. 11/143,986, filed on Jun. 2, 2005, now Pat. No. 7,300,657, which is a continuation of application No. PCT/EP03/51019, filed on Dec. 16, 2003.

(30) Foreign Application Priority Data

Dec. 17, 2002 (EP) .................................... 02102781
Jun. 12, 2003 (WO) ........................ PCT/EP03/50222

(51) Int. Cl.
| | |
|---|---|
| *A61K 39/00* | (2006.01) |
| *A61K 45/00* | (2006.01) |
| *C12N 15/00* | (2006.01) |
| *C12N 1/10* | (2006.01) |
| *C07H 21/04* | (2006.01) |
| *C07H 21/00* | (2006.01) |
| *A01N 63/00* | (2006.01) |
| *A01N 65/00* | (2009.01) |

(52) U.S. Cl. ............... 424/184.1; 435/320.1; 435/258.2; 536/23.7; 536/25.6; 424/278.1; 424/93.2; 424/93.1

(58) Field of Classification Search ........................ None
See application file for complete search history.

(56) References Cited

U.S. PATENT DOCUMENTS

| | | | |
|---|---|---|---|
| 6,306,625 B1 | 10/2001 | Jacobs et al. | |
| 7,192,759 B1 | 3/2007 | Pau et al. | |
| 7,300,657 B2 | 11/2007 | Pau et al. | |
| 7,387,894 B2 | 6/2008 | Pau et al. | |
| 7,491,395 B2 | 2/2009 | Stegmann et al. | |
| 7,504,248 B2 | 3/2009 | Marzio et al. | |
| 7,521,220 B2 | 4/2009 | Pau et al. | |
| 7,521,229 B2 | 4/2009 | Pau et al. | |
| 7,524,947 B2 | 4/2009 | Pau et al. | |
| 7,527,961 B2 | 5/2009 | Pau et al. | |
| 7,550,284 B2 | 6/2009 | Pau et al. | |
| 7,598,078 B2 | 10/2009 | Vogels et al. | |
| 7,604,960 B2 | 10/2009 | Hateboer et al. | |
| 7,696,330 B2 | 4/2010 | ter Meulen et al. | |
| 7,833,788 B2 | 11/2010 | Pau et al. | |
| 7,867,764 B2 | 1/2011 | Pau et al. | |
| 7,964,198 B2 | 6/2011 | Pau et al. | |
| 7,968,286 B2 | 6/2011 | Havenga et al. | |
| 8,097,453 B2* | 1/2012 | Pau et al. .................... | 435/320.1 |
| 2005/0164386 A1 | 7/2005 | Uytdehaag et al. | |
| 2007/0231860 A1 | 10/2007 | Uytdehaag et al. | |
| 2008/0014204 A1 | 1/2008 | ter Meulen et al. | |
| 2008/0050403 A1 | 2/2008 | Marzio et al. | |
| 2008/0131461 A1 | 6/2008 | Pau et al. | |
| 2008/0153083 A1 | 6/2008 | Vogels et al. | |
| 2010/0015176 A1 | 1/2010 | Havenga et al. | |
| 2010/0172917 A1 | 7/2010 | ter Meulen et al. | |
| 2011/0150930 A1 | 6/2011 | Pau et al. | |

FOREIGN PATENT DOCUMENTS

| | | |
|---|---|---|
| EP | 99 201 545.3 | 5/1999 |
| EP | 0 978 566 A2 | 2/2000 |
| EP | 1 054 064 | 11/2000 |
| WO | WO 93/10152 | 5/1993 |
| WO | WO96/26281 | 8/1996 |
| WO | WO 96/39178 | 12/1996 |
| WO | WO 97/00326 | 1/1997 |
| WO | WO 98/32842 | 7/1998 |
| WO | WO 98/50053 | 11/1998 |
| WO | WO 99/55132 | 11/1999 |
| WO | WO 99/64582 | 12/1999 |
| WO | WO 00/03029 | 1/2000 |
| WO | WO 00/52186 | 9/2000 |

(Continued)

OTHER PUBLICATIONS

Bruna-Romero et al., Detection of malaria live-stages in mice infected through the bite of a single Anopheles mosquito using a highly sensitive real-time PCR, International Journal of Parasitology, 2001, pp. 1499-1502, vol. 31.

De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, pp. 3940-3945, vol. 37, No. 12.

(Continued)

*Primary Examiner* — Vanessa L Ford
*Assistant Examiner* — Lakia Tongue
(74) *Attorney, Agent, or Firm* — TraskBritt

(57) ABSTRACT

Described are vaccines against malarial infections, which are based on recombinant viral vectors, such as alpha viruses, adenoviruses, or vaccinia viruses. The recombinant viral-based vaccines can be used to immunize against different *Plasmodium* infections, such as infections by *P. falciparum* or *P. yoelii*. Codon-optimized circumsporozoite genes are disclosed. Replication-defective adenoviruses may be used, derived from serotypes that encounter low titers of neutralizing antibodies. Also described is the use of different adenoviral serotypes that are administered to elicit a strong immune response, either in single vaccination set-ups or in prime-boost set-ups in which compositions based on different serotypes can be applied.

15 Claims, 11 Drawing Sheets

FOREIGN PATENT DOCUMENTS

| | | |
|---|---|---|
| WO | WO 00/70071 | 11/2000 |
| WO | WO 01/02607 | 1/2001 |
| WO | WO 01/05945 | 1/2001 |
| WO | WO 01/07571 | 2/2001 |
| WO | WO 02/22080 | 3/2002 |
| WO | WO 02/24730 | 3/2002 |
| WO | WO 02/40665 | 5/2002 |
| WO | WO 03/077859 | 9/2003 |
| WO | WO 2004/037189 A2 | 5/2004 |
| WO | WO 2004/055187 | 7/2004 |

OTHER PUBLICATIONS

Gandon et al., Imperfect vaccines and the evolution of pathogen virulence, Nature, Dec. 13, 2001, pp. 751-756, vol. 414.

Kurtis et al., Pre-erythrocytic immunity to *Plasmodium falciparum*: the case for an LSA-1 vaccine, Trends in Parasitology, May 2001, pp. 219-223, vol. 17, No. 5.

Lockyer et al., Wild isolates of *Plasmodium falciparum* show extensive polymorphism in T cell epitopes of the circumsporozoite protein, Molecular and Biochemical Parasitology, 1989, pp. 275-280, vol. 37.

Moran et al., Requirements for Glycosylphosphatidylinositol Attachment Are Similar but Not Identical in Mammalian Cells and Parasitic Protozoa, The Journal of Cell Biology, Apr. 1994, pp. 333-43, vol. 125, No. 2.

Nardin et al., A Totally Synthetic Polyoxime Malaria Vaccine Containing *Plasmodium falciparum* B Cells and Universal T Cell Epitopes Elicits Immune Responses in Volunteers of Diverse HLA Types, The Journal of Immunology, 2001, pp. 481-489, vol. 166.

Nussenzweig et at, Protective Inununity produced by the Injection of X-irradiateed Sporozoites of *Plasmodium berghei*, Nature, Oct. 14, 1967, pp. 160-162, vol. 216.

Rodrigues et al., Single Immunizing Dose of Recombinant Adenovirus Efficiently Induces CD8+ T Cell-Mediated Protective Immunity Against Malaria, The Journal of Immunology, 1997, pp. 1268-1274, vol. 158.

Romero et at, Cloned cytotoxic T cells recognize an epitope in the circumsporozoite protein and protect against malaria, Nature, Sep. 28, 1989, pp, 323-326, vol. 341.

Basler et al., "Sequence of the immunoregulatory early region 3 and flanking sequences of adenovirus type 35," Gene, 1996, pp. 249-254, vol. 170.

Benmohamed et al., "High immunogenicity in chimpanzees of peptides and lipopeptides derived from four new *Plasmodium falciparum* pre-erythrocytic molecules," Jun. 2000, pp. 2843-2855, vol. 18, No. 25.

Bruna-Romero et al., "Complete, long-lasting protection against malaria of mice primed and boosted with two distinct viral vectors expressing the same plasmodial antigen," Proc. Natl. Acad. Sci. USA, Sep. 25, 2001, pp. 11491-11496, vol. 98, No. 20.

Daubersies et al., "Protection against *Plasmodium falciparum* malaria in chimpanzees by immunization with the conserved pre-erythrocytic liver-stage antigen 3," Nature Medicine, Nov. 2000, pp. 1258-1263, vol. 6, No. 11.

Flomenberg et al., "Molecular Epidemiology of Adenovirus Type 35 Infections in Immunocompromised Hosts," The Journal of Infectious Diseases, Jun. 1987, pp. 1127-1134, vol. 155, No. 6.

Flomenberg et al., "Sequence and genetic Organization of Adenovirus Type 35 Early Region 3," Journal of Virology, Nov. 1988, pp. 4431-4437, vol. 62, No. 11.

Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.

Kang et al., "Molecular Cloning and Physical Mapping of the DNA of Human Adenovirus Type 35," Acta Microbiologica Hungarica, 1999, pp. 67-75, vol. 36, No. 1.

Krasnykh et al., "Generation of Recombinant Adenovirus Vectors with modified Fibers for Altering Viral Tropism," Journal of Virology, Oct. 1996, pp. 6839-3846, vol. 70, No. 10.

Miyahira et al., "Recombinant viruses expressing a human malaria antigen can elicit potentially protective immune CD8+ responses in mice," Proc. Natl. Acad. Sci. USA, Mar. 31, 1998, pp. 3954-3959, vol. 95, No. 7.

Nagata et al., "Codon Optimization Effect on Translational Efficiency of DNA Vaccine in Mammalian Cells: Analysis of Plasmid DNA Encoding a CTL Epitope Derived from Microorganisms," Aug. 2, 1999, pp. 445-451, vol. 261, No. 2.

Narum et al., "Codon Optimization of Gene Fragments Encoding *Plasmodium falciparum* Merzoite Proteins Enhances DNA Vaccine Protein Expression and Immunogenicity in Mice," Dec. 2001, pp. 7250-7253vol. 69, No. 12.

Crampton, et al.; Parasite vaccines: The new generation; ScienceDirect, Infection, Genetics and Evolution 7 (2007) 664-673.

Gilbert, et al.; Enhanced DC8 T cell immunogenicity and protective efficacy in a mouse malaria model using a recombinant adenoviral vaccine in heterologous prime-boost immunization regimes; Vaccine 20 (2002) 1039-1045.

Ophorst, et al. Expression and immunogenicity of the *Plasmodium falciparum* circumsporozoite protein: The role of the GPI signal sequence; ScienceDirect, Vaccine 25 (2007) 1426-1436.

Shott, et al. ; Adenovirus 5 and 35 vectors expressing *Plasmodium falciparum* circumsporozoite surface protein elicit potent antigen-specific cellular IFN-$\gamma$ and antibody responses in mice; Vaccine 26(2008) 2818-2823.

Genton et al., Safety and immunogenicity of a three-component blood-stage malaria vaccine (MSP1, MSP2, RESA) against *Plasmodium falciparum* in Papua New Guinean children, Vaccine 22, (2003) 30-41.

Becton Dickinson Integra™ Syringe product information, 2002.

Greenspan et al., Defining epitopes: It's not as easy as it seems, Nature Biotechnology, 1999, pp. 936-937, vol. 17.

Stewart et al. Priming with an Adenovirus 35-Circumsporozoite Protein (CS) Vaccine followed by RTS,S/ASO1B Boosting Significantly Improves Immunogenicity to *Plasmodium falciparum* CS Compared to That with Either Malaria Vaccine Alone, Infection and Immunity, May 2007, pp. 2283-2290, vol. 75, No. 5.

Lai et al., DNA and Cell Biology, Dec. 2002, 21(12): 895-913.

Notice of Opposition to a European Patent, Patent No. 1054064, by Cell Genesys Inc., dated Jul. 5, 2005.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Coat Protein Hexon," Journal of Virology, Aug. 1998, pp. 6875-6879, vol. 72, No. 8.

Scheiblhofer et al., "Removal of the circumsporosoite protein (CSP) glycosylphosphatidylinositol signal sequence from a CSP DNA vaccine enhances induction of CSP-specific Th2 type immune responses and improves protection against malaria infection," Eur. J. Immunol., Mar. 2001, pp. 692-698, vol. 31, No. 3.

Singh et al., "Advances in vaccine adjuvants," Nature Biotechnology, 1999, pp. 1075-1081, vol. 17.

Soares et al., "Malaria vaccine: roadblocks and possible solutions," Brazilian Journal of Medical and Biological Research, 1998, pp. 317-332, vol. 31.

Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.

Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Tine et al., "NYVAC-Pf7: a Poxvirus-Vectored, Multiantigen, Multistage Vaccine Candidate for *Plasmodium falciparum* Malaria," Infection and Immunity, 1996, pp. 3833-3844, vol. 64.

\* cited by examiner

```
AAGCTTGCCACCATGATGAGGAAACTGGCCATCCTGAGCGTGAGCAGCTTCCTGTTCGTGGA
GGCCCTGTTTCAGGAGTACCAGTGCTACGGCAGCAGCAACACCCGGTGCTGAACGAGC
TGAACTACGACAACGCCGGCACCAACCTGTACAACAGCGAGCTGGAGATGAACTACGGCAAG
CAGGAGAACTGGTACAGCCTGAAGAAGAACAGCGGGTCTCTGGGCGAGAACGACGACGGCAA
CAACAACAACGGCGACAACGGCGACAACGCGGAGGCAAGCACAAGCGGGACGGCAACAACG
AGGACAACGAGAAGCTGCGGAAGCCCAAGCACCCCAAGAAACTTAAGCAGCCCGACCGGCAAC
CCCGACCCCAAGCGCCAATGGACCCCAACGTGGACCCCAATCCTAATGTCGACCCCAATGC
CAATCCGAATGCTGATCCCAATGCCAAATGCGAATCTTAACCCAAATCGCTAACCCCAATGCCA
ATCCAAATGCCAATCCCAATGCCAAATGCGCTAATCCCGAACGCTAATCCGAACGCTAAT
CCTAATGCCAATCCCCAATGCTAACGCTAAATCCCGATCCTAACGCGCCTAATCCCGAACGCTAACCC
CAACGCAAATCCCAACGCTAACCCTGAACCAAAACGCAAATCCCGAATGCTAATGCCAACCCAA
ACGCCAACCCGAACCCGAATGCCAATCCCCAACGACCCCAACGAGCCCAATGCCAACCCAAAT
GCAAACCCAATGCAAACGGCAAACCCGATGCCCACAACAACCGAGGAGCCCAGTGGAACGTGGACGAGAACG
TCAGGGCAACGGCCAGGCCCACAACGGCCGTGAAGAACAACAGCCTGAGCACCGACAAGCACATCGAG
CCAAACGCCAACAACGCCCTGAAGATCCAGATGCCGGATCAGTTCAGTGCCAGCCGCAAGCCCAGGAGCCCCTGCAGCGTGACCTG
CAGTACCCAACGCTGAGCCCGGCAGCCCTGAGCACCTGAGCCCGCCAGCCCGAGTGGAGCCCAACGAGCCTGGCCAACAGCCCGACCAGCACGAG
CGGCAACGGCATTCAGTTGCCGGATCAAGCTGCAAGCCCGGATCAAGCCCAAGCCCAAGGACGAGCTGG
ACTACGAGAATGACATCGAGAAGAAGATCTGCAAGATGCAAGATGAAGTGCAGCAGCAGCGTTCAAC
GTGGTGAACAGCGCCATCGGCCTG
ATTATGTGCTGAGCTTCCTGTTCCTGAACTGAAGATCTGCTGATAAGGATCC
```

FIG. 2A

MMRKLAILSVSSFLFVEALFQEYQCYGSSNTRVLNELYDNAGTNLGNEDDGMNYGKQENWYSLKKNSRSLGENDDEKNNNGDNGREGKDEDKRDGPDDNEKLRKPHKKLKQPADGNPDPNDPNRNVDPNRKIQVRKICKHHIKEYLKVRIKPGPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNANPNKNANPNANPNANPNEPSDKHKEPKHIKDEYLNKKICKMEKCSSVFNVNS*

FIG. 2B

AAGCTTGCCACCATGATGAGGAAACTGGCCATCCTGAGCGTGAGCAGCTTCCTGTTCGTG
GAGGCCCTGTTTCAGGAGTACCAGTGCTACGGCAGCAGCAACACCCGGGTGCTGAAC
GAGCTGAACTACGACAACGCCGGCACCAACCTGTACAACGAGCTGGAGATGAACTACTAC
GGCAAGCAGGAGAACAACAGCGCCGGTCTCTGGGCGAGAACGAC
GACGGCAACAACAACGAGGACAACGAGAAGCACAAGAAACTTAAGCAGCCC
GGCAACAACGAGGACAACGAGAAGCTGCGGAAGCCCAAGCACAAGAAACTTAAGCAGCCC
GCCGACGGCAACCCCGACCCCAACGCCCAACGTGGACCCCAACGCCAATCCTAAT
GTCGACCCCCAATGCCAATCCCGAATCCCAATGCCAATCCTAACGCTAACCCCCAAT
GCCAACCCAAATGCCAATCCCAAATGCCAATCCCAACGCCAATCCCAAACGCAAACCCTAAT
GCTAATCCAAAACGCTAATCCTAACGCTAACCCCCAATGCTAACCCCAAACGTCGATCCTAAC
GCAAATCCGAATGCCAATCCCAACGCTAACGCTAACCCCGAACGCTAACCCGAAT
GCCAATCCGAATGCCAATCCCAACGCTAATGCCAACCCGAACGCTAACCCCGAAT
GCTAATCCTAACGCCAAATGCCAAACAAGAACAATCAGGGCAACAACGCCAACATCCCAAC
GCCAATCCTAACCCGGAACGTGGACGAGAACGCGCCAACAGCGCCGTGAAGAACAACAAC
GACCCCAACCGGAACGTGGACGAGAACGCACATCAAGGAGTACCTGAACAAGATCCAGAACAGCCTG
AACGGAGAGCCCAGCGACCCCTGCAGCGTGCCGGCAACGGCATTCAGGTGCGGATCAAG
AGCACCGAGTGGAGCCCCTGCAGCGTGCCGGCAACGGCATTCAGGTGCGGATCAAG
CCCGGCAGCGCCAACAAGCCCAAGGACGAGCTGGACTACGCCAATGACATCGAGAAGAAG
ATCTGCAAGATGGAGAAGTGCAGCAGCGTGTTCAACGTGGTGAACTCCTGATAAGATCT
GCTGATAAGGATCC

FIG. 3A

[Figure shows a protein amino acid sequence displayed as a grid of single-letter codes, rotated 90°. The sequence contains characteristic collagen-like G-X-Y repeats (e.g., GAPQGPGAPQ, GPPQ) in its central region, flanked by non-repetitive N-terminal and C-terminal domains, and terminates with a stop codon (*).]

FIG. 3B

AAGCTTGCTAGCCAACCATGAAGAAGTGCACCATCCTGCTGGTGGTGGCCAGCCTGCTGCT
GGTGGACAGCCTGCTGCCCGGCTACGGCCCAGAACAAGAGCGTGCAGGCGTGCCAGCGGAA
CCTGAACGAGCTGTGCTACAAGATTTACAACCAAGCTGTACCACGTGCTGTGAA
CAGCAAGAACGGCAAGATTTACAAGATTTACAACCGAACATCGTGAACCGGCTGCTGGGCGACGC
CCTGAACGGCAAGCCCGAGGAGAAGGACGAGAAGACGACCCCAAGGACGGCAACAAGGA
CGACCTGCCCAAGGAGGAGAAGAAAGACGATCTGCCTAAGGAGGAAAAAAGGACGA
TCCTCCTAAGGACCCCAAGAAGACGATCCTCCAAAGAGGCCCAGAACAAGCTGAA
CCAGCCCGTGGTGGCCGACGAGAACGTGGACCAGGCCCCTGGCCCCCTCAGGGCCC
CGGGGCCCCTCAGGGACCCTGGAGCCCTCAAGGACCCCGAGCCCCCAGGGACCTGG
CGCTCCTCAGGGACCCGGCGCCCCACAAGGTCCCCAGGGCCTCCCTCAGGGTCCCCAGGGC
ACCCCCAGGGCCCAGGCCACCAGCCCCCTGGGGCCCCACAAGGGCCACAGCCCAGGACC
TCAGGGGCCTGGCGCACCCCAGGAGCCCCCAGCAGCCCTCAGCAGCCCACACAGCCAGCA
AGGGCCCTGGGCACCCCCAACAGCCTCCCCAACAACAACAACAACAACGGCAACAACAGCCC
CCAGCCCGACGGCCAGCGCCAGCAGATCCTGAGTTCGTGAAGCAGATCAGCAGCCAACT
CTACGTGCCAGGAGTGGAGCCAGTGCAGCCTGCGCGTGACCTGCGGCCAGTGCGGGGTGCCGGAA
GACCGAGGAGTGGAGCCAGTGCAGCCTGCGCGTGACCTGCGGCCAGTGCGGGGTGCCGGAA
GCGGAAGAACGTGAACAAGCAGCCCGAGAACCTGACCCTGGAGGACATCGACGACCGA
GATCTGCAAGATGACAAGTGCAGCATCTTCAACATCGTGAGCAACACAGCCCTGGG
CTGAAGATCTGCTGATAAGTTTAAACGGATCC

RECOMBINANT VIRAL-BASED MALARIA VACCINES

CROSS-REFERENCE TO RELATED APPLICATIONS

This application is a divisional of U.S. patent application Ser. No. 12/928,044, filed Dec. 1, 2010, now U.S. Pat. No. 8,097,453, issued Jan. 17, 2012, which is a continuation of U.S. Ser. No. 11/975,396, filed Oct. 18, 2007, now U.S. Pat. No. 7,867,764, issued Jan. 11, 2011, which is a divisional of U.S. Ser. No. 11/607,366, filed Dec. 1, 2006, now U.S. Pat. No. 7,387,894, issued Jun. 17, 2008, which is a divisional of U.S. patent application Ser. No. 11/143,986, filed Jun. 2, 2005, now U.S. Pat. No. 7,300,657, issued Nov. 27, 2007, which is a continuation of PCT International Patent Application No. PCT/EP2003/051019, filed on Dec. 16, 2003, designating the United States of America, and published, in English, as PCT International Publication No. WO 2004/055187 A1 on Jul. 1, 2004, which, in turn, claims priority under Article 8 of the PCT to PCT International Patent Application No. PCT/EP03/50222, filed on Jun. 12, 2003, which, in turn, claims priority to European Patent Application Serial No. 02102781.8 filed Dec. 17, 2002, the disclosures of each of which are hereby incorporated herein in their entirety by this reference.

TECHNICAL FIELD

The disclosure generally relates to the field of medicine and biotechnology. More particularly, the disclosure relates to the use of a recombinantly produced viral vector as a carrier of an antigenic determinant selected from a group of malaria pathogens for the development of a vaccine against malaria infections.

BACKGROUND

Malaria currently represents one of the most prevalent infections in tropical and subtropical areas throughout the world. Per year, malaria infections lead to severe illnesses in hundreds of million individuals worldwide, while it kills 1 to 3 million people, primarily in developing and emerging countries every year. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus *Plasmodium*. Four species of *Plasmodium* protozoa (*P. falciparum, P. vivax, P. ovale* and *P. malariae*) are responsible for the disease in man; many others cause disease in animals, such as *P. yoelii* and *P. berghei* in mice. *P. falciparum* accounts for the majority of infections and is the most lethal type ("tropical malaria"). Malaria parasites have a life cycle consisting of several stages. Each stage is able to induce specific immune responses directed against the corresponding occurring stage-specific antigens.

Malaria parasites are transmitted to man by several species of female *Anopheles* mosquitoes. Infected mosquitoes inject the "sporozoite" form of the malaria parasite into the mammalian bloodstream. Sporozoites remain for a few minutes in the circulation before invading hepatocytes. At this stage, the parasite is located in the extra-cellular environment and is exposed to antibody attack, mainly directed to the "circum-sporozoite" (CS) protein, a major component of the sporozoite surface. Once in the liver, the parasites replicate and develop into so-called "schizonts." These schizonts occur in a ratio of up to 20,000 per infected cell. During this intracellular stage of the parasite, main players of the host immune response are T-lymphocytes, especially CD8+ T-lymphocytes (Romero et al. 1998). After about one week of liver infection, thousands of so-called "merozoites" are released into the bloodstream and enter red blood cells, becoming targets of antibody-mediated immune response and T-cell secreted cytokines. After invading erythrocytes, the merozoites undergo several stages of replication and transform into so-called "trophozoites" and into schizonts and merozoites, which can infect new red blood cells. This stage is associated with overt clinical disease. A limited amount of trophozoites may evolve into "gametocytes," which is the parasite's sexual stage. When susceptible mosquitoes ingest erythrocytes, gametocytes are released from the erythrocytes, resulting in several male gametocytes and one female gametocyte. The fertilization of these gametes leads to zygote formation and subsequent transformation into ookinetes, then into oocysts, and finally into salivary gland sporozoites.

Targeting antibodies against gametocyte stage-specific surface antigens can block this cycle within the mosquito mid gut. Such antibodies will not protect the mammalian host but will reduce malaria transmission by decreasing the number of infected mosquitoes and their parasite load.

Current approaches to malaria vaccine development can be classified according to the different stages in which the parasite can exist, as described above. Three types of possible vaccines can be distinguished:

Pre-erythrocytic vaccines, which are directed against sporozoites and/or schizont-infected cells. These types of vaccines are primarily CS-based, and should ideally confer sterile immunity, mediated by humoral and cellular immune response, preventing malaria infection.

Asexual blood-stage vaccines, which are designed to minimize clinical severity. These vaccines should reduce morbidity and mortality and are meant to prevent the parasite from entering and/or developing in the erythrocytes.

Transmission-blocking vaccines, which are designed to hamper the parasite development in the mosquito host. This type of vaccine should favor the reduction of population-wide malaria infection rates.

Next to these vaccines, the feasibility of developing malaria vaccines that target multiple stages of the parasite life cycle is being pursued in so-called multi-component and/or multi-stage vaccines. Currently, no commercially available vaccine against malaria is available, although the development of vaccines, against malaria has already been initiated more than 30 years ago: immunization of rodents, non-human primates and humans with radiation-attenuated sporozoites conferred protection against a subsequent challenge with sporozoites (Nussenzweig et al. 1967; Clyde et al. 1973). However, the lack of a feasible large-scale culture system for the production of sporozoites prevents the widespread application of such vaccines.

To date, the most promising vaccine candidates tested in humans have been based on a small number of sporozoite surface antigens. The CS protein is the only *P. falciparum* antigen demonstrated to consistently prevent malaria when used as the basis of active immunization in humans against mosquito-borne infection, albeit it at levels that is often insufficient. Theoretical analysis has indicated that the vaccine coverage, as well as the vaccine efficiency, should be above 85% or, otherwise, mutants that are more virulent may escape (Gandon et al. 2001).

One way of inducing an immune response in a mammal is by administering an infectious carrier that harbors the antigenic determinant in its genome. One such carrier is a recombinant adenovirus, which has been replication-defective by removal of regions within the genome that are normally essential for replication, such as the E1 region. Examples of recombinant adenoviruses that comprise genes encoding antigens are known in the art (PCT International Patent Publication WO 96/39178), for instance, HIV-derived antigenic components have been demonstrated to yield an immune response if delivered by recombinant adenoviruses (WO 01/02607 and WO 02/22080). Also for malaria, recombinant adenovirus-based vaccines have been developed. These vectors express the entire CS protein of *P. yoelii*, which is a mouse-specific parasite, and these vectors have been shown to be capable of inducing sterile immunity in mice in response to a single immunizing dose (Bruña-Romero et al. 2001a). Furthermore, a similar vaccine vector using CS from *P. berghei* was recently shown to elicit long-lasting protection when used in a prime-boost regimen, in combination with a recombinant vaccinia virus (Gilbert et al. 2002) in mice. It has been demonstrated that CD8+ T-cells primarily mediate the adenovirus-induced protection. It is unlikely the *P. yoelii*- and *P. berghei*-based adenoviral vectors would work well in humans, since the most dramatic malaria-related illnesses in humans are not caused by these two parasites. Moreover, it is preferred to have a vaccine which is potent enough to generate long-lasting protection after one round of vaccination, instead of multiple vaccination rounds using either naked DNA injections and/or vaccinia-based vaccines as boosting or priming agents.

Despite all efforts to generate a vaccine that induces an immune response against a malaria antigenic determinant and protects from illnesses caused by the malaria parasite, many vaccines do not fulfill all requirements as described above. Whereas some vaccines fail to give a protective efficiency of over 85% in vaccinated individuals, others perform poorly in areas, such as, production or delivery to the correct cells of the host immune system.

BRIEF SUMMARY OF THE INVENTION

Described are different kinds of replication-defective recombinant viral vectors comprising a heterologous nucleic acid encoding an antigenic determinant of several *Plasmodium* protozoa. The viral vectors may comprise nucleic acids encoding the circumsporozoite (CS) protein of *P. falciparum* and *P. yoelii*. The viral vector may be an adenovirus, e.g., based on a serotype that is efficient in delivering the gene of interest, that encounters low numbers of neutralizing antibodies in the host and that binds to the relevant immune cells in an efficient manner. In certain embodiments, the CS protein is generated such that it will give rise to a potent immune response in mammals, e.g., humans. In one aspect, the expression of the protein is elevated due to codon optimization and thus altering the codon usage such that it fits the host of interest. The novel CS proteins of the invention are depicted in FIGS. 1A (SEQ ID NO:3 of the incorporated herein SEQUENCE LISTING), 2A (SEQ ID NO:6) and 3A (SEQ ID NO:9), while the codon-optimized genes encoding the proteins are depicted in FIGS. 1B (SEQ ID NO:1), 2B (SEQ ID NO:4) and 3B (SEQ ID NO:7), respectively.

Also described are vaccine compositions comprising a replication-defective recombinant viral vector as described herein and a pharmaceutically acceptable carrier, further comprising, e.g., an adjuvant. Furthermore, also described is the use of a vaccine composition as disclosed herein in the therapeutic, prophylactic or diagnostic treatment of malaria.

BRIEF DESCRIPTION OF THE SEVERAL VIEWS OF THE DRAWINGS

FIG. 1 shows the newly synthesized clone 02-148 (pCR-script.Pf), which is based on a range of known *Plasmodium falciparum* genes and which encodes the novel circumsporozoite protein (A) (SEQ ID NO:3), plus the codon-optimized nucleic acid molecule (B) (SEQ ID NO:1). SEQ ID NO:2 is the translated protein product translated from the Coding Sequence of SEQ ID NO:1 as generated by PatentIn 3.1. SEQ ID NO:2 is identical to SEQ ID NO:3 in content.

FIG. 2 shows the amino acid molecule (A) (SEQ ID NO:6) and nucleic acid molecule (B) (SEQ ID NO:4) of synthetic clone named 02-659 (pf-aa-sub), which is the circumsporozoite gene of the *P. falciparum* strain 3D7, lacking the C-terminal 14 amino acids. SEQ ID NO:5 is the translated protein product translated from the Coding Sequence of SEQ ID NO:4 as generated by PatentIn 3.1. SEQ ID NO:5 is identical to SEQ ID NO:6 in content.

FIG. 3 shows the amino acid molecule (A) (SEQ ID NO:9) and nucleic acid molecule (B) (SEQ ID NO:7) of the codon-optimized circumsporozoite gene of *P. yoelii*. SEQ ID NO:8 is the translated protein product translated from the Coding Sequence of SEQ ID NO:7 as generated by PatentIn 3.1. SEQ ID NO:8 is identical to SEQ ID NO:9 in content.

FIG. 4 shows the (A) cellular immune response and the (B) humoral immune response in mice upon immunization with Ad5- and Ad35-based vectors harboring the *P. yoelii* circumsporozoite gene, administered via two routes: intramuscular and subcutaneous in different doses.

FIG. 5 shows the inhibition in mice of a *P. yoelii* sporozoite challenge following immunization with Ad5- and Ad35-based vectors harboring the *P. yoelii* circumsporozoite gene, administered in different doses, depicted in percentage of inhibition (A), and in the presence of parasite-specific RNA molecules in the liver (B).

FIG. 6 shows the cellular immune response raised by immunization with an Ad5-based vector harboring the full-length *P. falciparum* circumsporozoite gene and two deletion mutants, administered in different doses.

DETAILED DESCRIPTION OF THE INVENTION

Described is the use of recombinant viruses as carriers of certain specific antigenic determinants selected from a group of malaria antigens. In various embodiments, provided is a solution to at least a part of the problems outlined above for existing vaccines against malaria.

Also described is a replication-defective recombinant viral vector comprising a heterologous nucleic acid encoding an antigenic determinant of *P. falciparum*. In certain embodiments, the viral vector is an adenovirus, an alphavirus or a vaccinia virus. In certain embodiments, the viral vector is an adenovirus, wherein the adenovirus may be derived from a serotype selected from the group consisting of Ad5, Ad11, Ad26, Ad34, Ad35, Ad48, Ad49, and Ad50. In one aspect, the replication-defective recombinant viral vector as described herein comprises an antigenic determinant that is the circumsporozoite (CS) protein or an immunogenic part thereof. The heterologous nucleic acid may be codon optimized for elevated expression in a mammal, e.g., a human. Codon optimization is based upon the required amino acid content, the general optimal codon usage in the mammal of interest and a number of provisions of aspects that should be avoided to

Figure 4A:
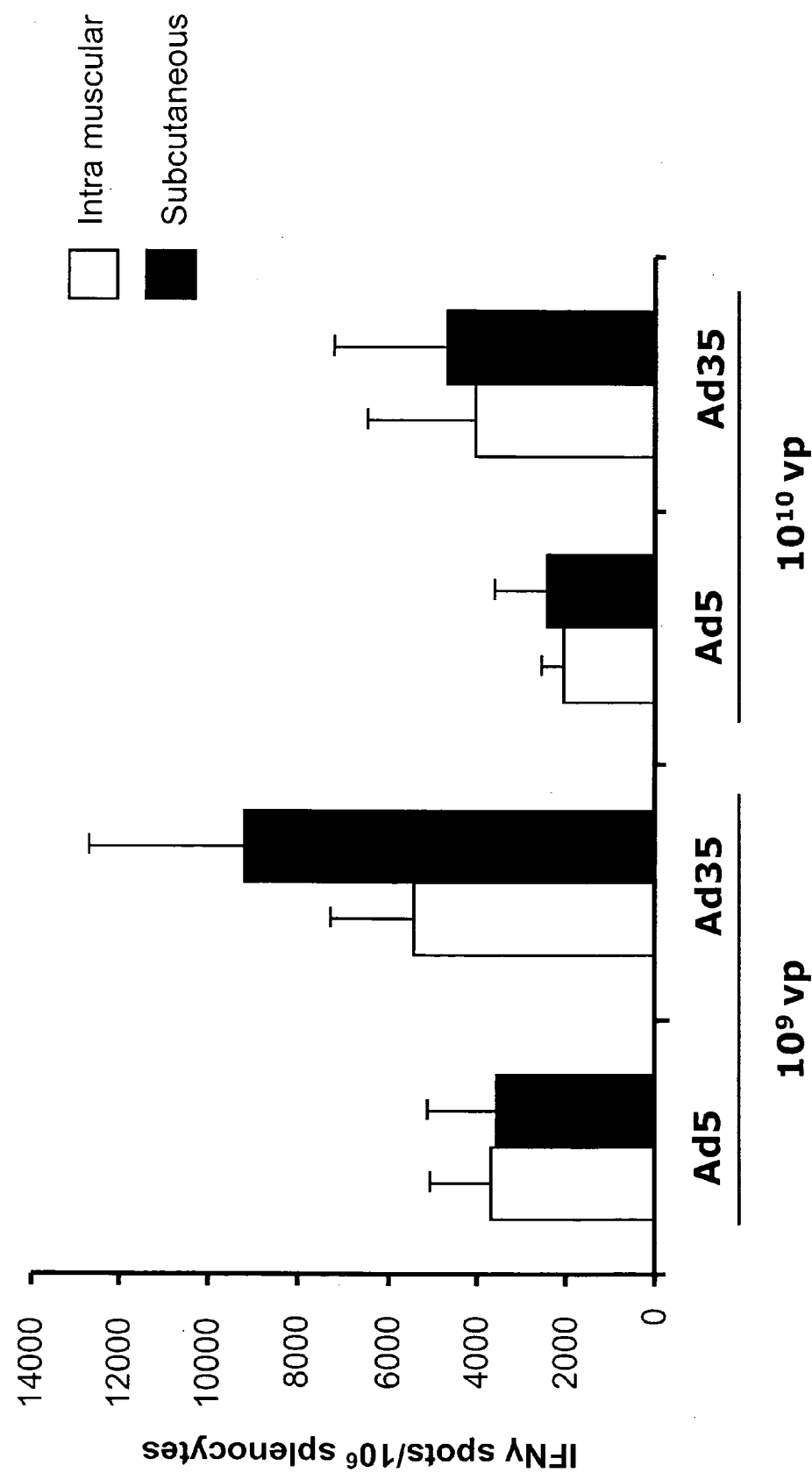

ensure proper expression. Such aspects may be splice donor or acceptor sites, stop codons, Chi-sites, poly(A) stretches, GC- and AT-rich sequences, internal TATA boxes, etc.

Figure 1A:
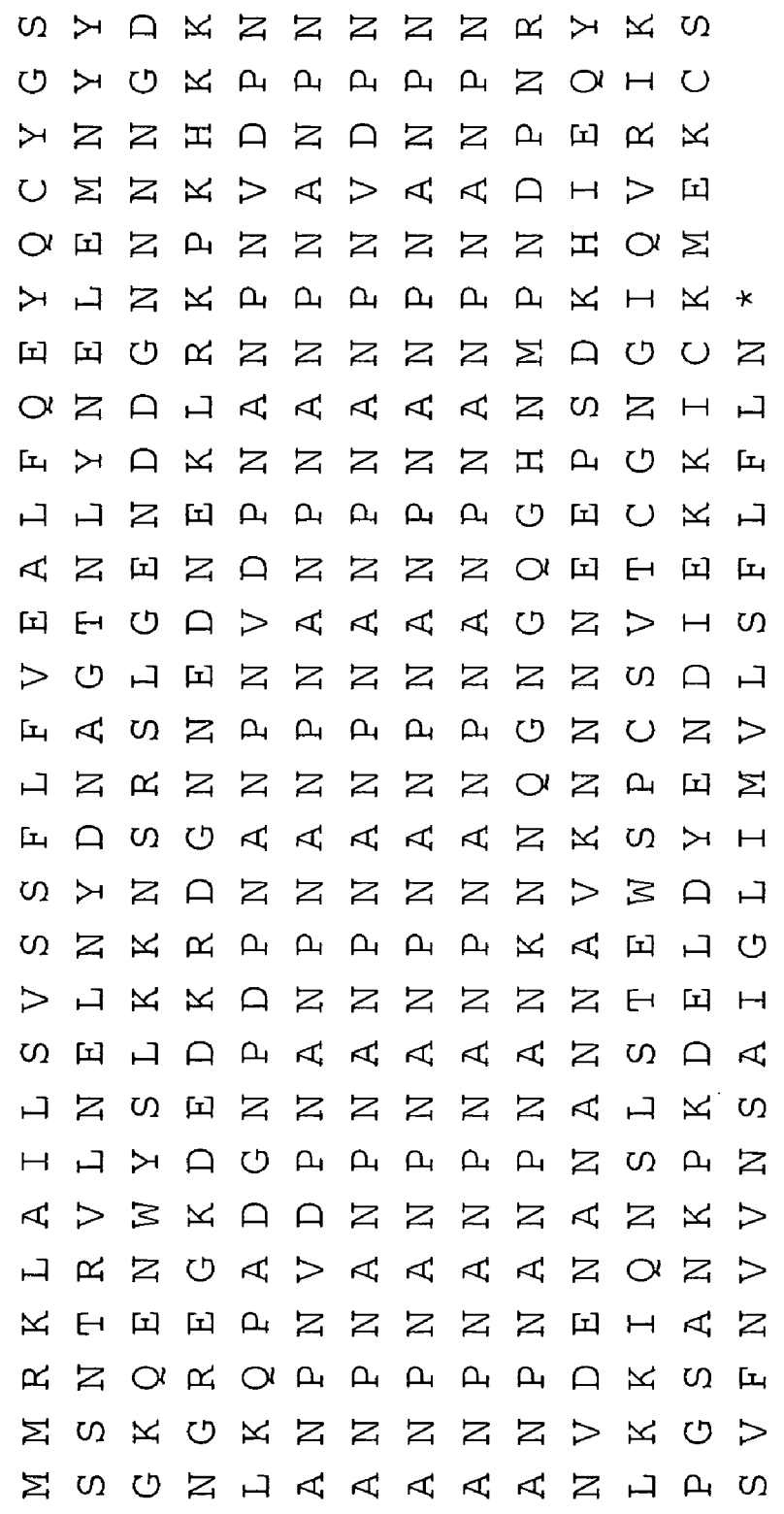

In certain embodiments, the disclosure relates to a replication-defective recombinant viral vector as described herein, wherein the adenine plus thymine content in the heterologous nucleic acid, as compared to the cytosine plus guanine content, is less than 87%, preferably less than 80%, more preferably less than 59% and most preferably equal to approximately 45%. The invention provides, in certain embodiments, a replication-defective recombinant viral vector, wherein the circumsporozoite protein is the circumsporozoite protein as depicted in FIG. 1A and in another embodiment, a codon-optimized heterologous nucleic acid as depicted in FIG. 1B. The proteins can be in a purified form, but also expressed in vivo from nucleic acid delivery vehicles such as the recombinant viral vectors of the invention. In a purified form, such proteins can be applied in other types of vaccines, wherein the protein is, for instance, enclosed in liposomes or other carriers used in the art. The nucleic acid can be cloned into other vectors than as disclosed herein, but also be applied as naked DNA in other vaccine settings.

In another embodiment, the invention relates to a replication-defective recombinant viral vector as described herein, wherein the circumsporozoite protein, or the immunogenic part thereof, is lacking a functional GPI anchor sequence.

Apart from the use of new genes and proteins that can be applied for use in humans, also disclosed are novel genes that may be used in humans as well as in other mammals. Therefore, the disclosure also relates to a replication-defective recombinant viral vector comprising a heterologous nucleic acid encoding the circumsporozoite protein of *Plasmodium yoelii*, wherein the nucleic acid is codon optimized for elevated expression in a mammal.

In certain embodiments, the viral vector is an adenovirus, an alphavirus, or a vaccinia virus, and preferably a recombinant adenovirus, which may be selected from the group consisting of Ad5, Ad11, Ad26, Ad34, Ad35, Ad48, Ad49, and Ad50. As in *P. falciparum*, it is also for *P. yoelii* preferred to use a codon-optimized gene for proper expression in the host of interest. Therefore, in certain embodiments, the adenine plus thymine content in the nucleic acid, as compared to the cytosine plus guanine content, is less than 87%, preferably less than 80%, more preferably less than 59% and most preferably equal to approximately 45%.

Also provided is a replication-defective recombinant viral vector as described herein, wherein the circumsporozoite protein is the circumsporozoite protein as depicted in FIG. 3A, while in another embodiment, a replication-defective recombinant viral vector is provided, wherein the nucleic acid is the nucleic acid depicted in FIG. 3B. In one aspect, the circumsporozoite protein, or the immunogenic part thereof, may lack a functional GPI anchor sequence.

Also disclosed is an isolated nucleic acid encoding a circumsporozoite protein of *Plasmodium falciparum* as depicted in FIG. 1B, wherein the nucleic acid is codon optimized, and to an isolated nucleic acid encoding a circumsporozoite protein of *P. falciparum* strain 3D7, as depicted in FIG. 2B, wherein the nucleic acid is codon optimized. Such isolated nucleic acids can be applied in subcloning procedures for the generation of other types of viral-based vaccines, apart from the types as disclosed herein. Furthermore, such isolated nucleic acids can be used for naked DNA vaccines or in cloning procedures to generate vectors for in vitro production of the encoded protein, which, in itself, can be further used for vaccination purposes and the like. The production can be in all kinds of systems, such as bacteria, yeasts or mammalian cells known in the art.

In another embodiment, an isolated nucleic acid encoding a circumsporozoite protein of *P. yoelii* as depicted in FIG. 3B is provided, wherein the nucleic acid is codon optimized. Furthermore, a vaccine composition comprising a replication-defective recombinant viral vector as described herein and a pharmaceutically acceptable carrier is provided. Pharmaceutically acceptable carriers are well known in the art and used extensively in a wide range of therapeutic products. Preferably, carriers are applied that work well in vaccines. More preferred are vaccines further comprising an adjuvant. Adjuvants are known in the art to further increase the immune response to an applied antigenic determinant. The invention also relates to the use of a vaccine composition as described herein in the therapeutic, prophylactic or diagnostic treatment of malaria.

Another embodiment relates to a method of treating a mammal for a malaria infection or preventing a malaria infection in a mammal, the method comprising (in either order or simultaneously) the steps of administering a vaccine composition as described herein and administering a vaccine composition comprising at least one purified malaria-derived protein or peptide. Also described is a method of treating a mammal for a malaria infection or preventing a malaria infection in a mammal, the method comprising (in either order or simultaneously) the steps of administering a vaccine composition comprising a replication-defective recombinant viral vector comprising a malaria circumsporozoite antigen as described herein and administering a vaccine composition comprising a replication-defective recombinant viral vector comprising another antigen, such as LSA-1 or LSA-3 as described herein.

The advantages of the invention are multi-fold. Next to the knowledge that recombinant viruses, such as recombinant adenoviruses, can be produced to very high titers using cells that are considered safe and that can grow in suspension to very high volumes, using medium that does not contain any animal- or human-derived components, the invention combines these features with a vector harboring the circumsporozoite gene of *P. falciparum*. *P. falciparum* is the parasite that causes tropical malaria. Moreover, the gene has been codon optimized to give an expression level that is suitable for giving a proper immune response in humans. The invention provides a vaccine against malaria infections, making use of, for instance, adenoviruses that do not encounter high titers of neutralizing antibodies. Examples of such adenoviruses are serotype 11 and 35 (Ad11 and Ad35, see WO 00/70071 and WO 02/40665).

The nucleic acid content between the malaria-causing pathogen, such as *P. falciparum*, and the host of interest, such as *Homo sapiens*, is very different. Now provided is a solution to some of the disadvantages of vaccines known in the art, such as, expression levels that are too low to elicit a significant immune response in the host of interest, e.g., humans.

Recombinant viral vectors have been used in vaccine set-ups. This has been demonstrated for vaccinia-based vaccines and for adenovirus-based vaccines. Moreover, a platform based on alphaviruses is being developed for vaccines as well. In certain embodiments, the invention relates to the use of recombinant adenoviruses that are replication defective through removal of at least part of the E1 region in the adenoviral genome, because the E1 region is required for replication, transcription, translation and packaging processes of newly made adenoviruses. E1-deleted vectors are generally produced on cell lines that complement for the deleted E1 functions. Such cell lines and the use thereof for the production of recombinant viruses have been described extensively and are well known in the art. Preferably, PER.C6® producer cells, as represented by the cells deposited under ECACC no. 96022940 at the European Collection of Animal Cell Cultures (ECACC) at the Centre for Applied Microbiology and Research (CAMR, UK), are being used in the cell line to prevent the production of replication-competent adenoviruses ("rca"). In another preferred embodiment, cells are being applied that support the growth of recombinant adenoviruses other than those derived from adenovirus serotype 5 ("Ad5"). Reference is made to publications WO 97/00326, WO 01/05945, WO 01/07571, WO 00/70071, WO 02/40665 and WO 99/55132, for methods and means to obtain rca-free adenoviral stocks for Ad5, as well as for other adenovirus serotypes.

Adenoviral-based vectors that have been used in the art mainly involved the use of Ad5 vectors. However, as has been described (WO 00/03029, WO 02/24730, WO 00/70071, WO 02/40665 and in other reports in the art), administration of Ad5 and efficient delivery to the target cells of interest responsible for sufficient immunogenic responses, is hampered by the presence of high titers of neutralizing antibodies circulating in the bloodstream if a subject previously encountered an Ad5 infection. It has been investigated what serotypes are better suited for therapeutic use and it turned out that a limited number of serotypes encountered neutralizing antibodies in only a small percentage of individuals in the human population. These experiments have been described in WO 00/70071. Therefore, in certain embodiments, the invention relates to the use of adenovirus serotype 11, 26, 34, 35, 48 and 50 and, more preferably, to Ad11 and Ad35, since these serotypes encountered no neutralizing antibodies in the vast majority of tested samples.

Apart from avoiding the presence of neutralizing antibodies directed against certain serotypes, it might also be beneficial to target the replication-deficient recombinant viral vectors to a certain subset of cells involved in the immune response. Such cells are, for instance, dendritic cells. It was found that certain adenovirus serotypes, such as Ad16, Ad35, and Ad50, carry capsid proteins that specifically bind to certain receptors present on dendritic cells (WO 02/24730). Ad5 is a serotype that is mainly homing to the liver, which may be a disadvantage if sufficient numbers of viral particles should infect cells of the immune system. It was found that at least in in vitro experiments, some of the serotypes different from Ad5 could infect dendritic cells multi-fold better than Ad5, suggesting that also in vivo the delivery to such cells is more efficient. It still remains to be seen whether this in vitro to in vivo translation holds up and if serotypes other than Ad5 will give rise to the required protection level. It is also part of the invention to provide the serotypes of choice, as far as neutralizing antibodies are concerned, with capsid proteins, such as the fiber or a part thereof from a serotype that is able to selectively recognize dendritic cells. It must be noted here that in the published documents WO 00/03029, WO 02/24730, WO 00/70071, and WO 02/40665, Ad50 was mistakenly named Ad51. The Ad51 serotype that was referred to in the mentioned publications is the same as serotype Ad50 in a publication by De Jong et al. (1999), wherein it was denoted as a B-group adenovirus. For the sake of clarity, Ad50 as used herein, is the B-group Ad50 serotype as mentioned by De Jong et al. (1999).

It is now known that a first administration with a specific adenoviral serotype elicits the production of neutralizing antibodies in the host against that specific vector. Thus, it is desirable to use in a subsequent setting (a follow-up boost or in the administration of another, non-related vaccine) a composition based on a different adenovirus serotype, which is not neutralized by antibodies raised in the first administration. Therefore, the invention further relates to methods for vaccinating mammalian individuals in which a priming vaccine composition comprises a replication-defective recombinant adenovirus of a first serotype, while in a boosting vaccine composition, a replication-defective recombinant adenovirus of a second serotype are used. Prime/boost settings have been described in more detail in international patent applications PCT/NL02/00671 and PCT/EP03/50748 (not published). These applications relate to the use of a recombinant adenovirus vector of a first serotype for the preparation of a medicament for the treatment or prevention of a disease in a human or animal treated with a recombinant adenovirus vector of a second serotype, wherein the first serotype is different from the second serotype, and wherein the first serotype is selected from the group consisting of: Ad11, Ad26, Ad34, Ad35, Ad46, and Ad49, and wherein the second serotype is preferably adenovirus serotype 5. Thus, it relates to the use of different adenoviral serotypes that encounter low pre-existing immunities in subjects that are to be treated. Preferred examples of such serotypes are the recombinant mentioned, wherein Ad5 is not excluded for individuals that have never experienced an Ad5 infection. The settings described and claimed in the applications mentioned above relate to the use of adenoviral vectors carrying transgenes, such as those from measles, or gag from HIV (for treatment of humans) or SIV (for treatment and studies in monkeys).

One non-limiting example of a prime-boost set-up towards Malaria is a setting in which, next to different adenovirus serotypes, different antigenic determinants may also be used. One non-limiting example of an antigen different from CS is the Liver-Specific Antigen 1 (LSA-1, Kurtis et al. 2001). Such set-ups are at least for one reason useful, namely, that the CS antigen is expressed mainly during the blood stage of the parasite, while its expression goes down in the liver stage. For LSA-1, this situation is more or less the opposite; it is expressed to low levels during the blood stage, but is highly expressed during the liver stage. Although one could use both antigens in subsequent administrations, it may also be used at the same time to provide protection against the parasite at the blood stage as well as at the liver stage. In a further embodiment of the invention, both antigens may be delivered by one adenovirus serotype (either cloned together in the same vector or separately in separate vectors of the same serotype). In another embodiment, both antigens are delivered by different serotypes that may be delivered at the same time or separately in time, for instance, in a prime-boost setting. The vaccines hereof may also be used in settings in which prime-boosts are being used in combination with naked DNA or other delivery means, unrelated to the replication-defective viral vectors hereof, such as purified proteins or peptides. Examples of such proteins that may be used in prime-boosts (Ad/protein; protein/Ad; protein/Ad/Ad; Ad/protein/Ad; Ad/Ad/protein, etc) are CS, LSA-1, LSA-3, MSP-1, MSP-119, MSP-142 (see below), or the hepatitis B particles containing and CS-derived vaccine composition known as RTS,S (see Gordon et al. 1995, U.S. Pat. No. 6,306,625 and WO 93/10152).

Although the invention is exemplified herein with the use of adenoviruses, it is to be understood that the invention is by no means intended to be limited to adenoviruses but also relates to the use of other recombinant viruses as delivery vehicles. Examples of viruses that can also be used for administering the antigenic determinants of the invention are poxviruses (vaccinia viruses, such as MVA) and flaviviruses such as alphaviruses. Non-limiting examples of alphaviruses that may be applied for delivering the immunogenic *Plasmodium* components of the invention are: Ndumu virus, Buggy Creek virus, Highland J. virus, Fort Morgan virus, Babanki virus, Kyzylagach virus, Una virus, Aura virus, Whataroa virus, Bebaru virus, South African Arbovirus No. 86, Mayaro virus, Sagiyama virus, Getah virus, Ross River virus, Barmah Forest virus, Chikungunya virus, O'nyong-nyong virus, Western Equine Encephalitis virus (WEE), Middelburg virus, Everglades virus, Eastern Encephalitis virus (EEE), Mucambo virus and Pixuna virus. Preferably, when an alphavirus is the virus of choice, Semliki Forest Virus, Sindbis virus or Venezuelan Equine Encephalitis virus are applied.

A sequence is "derived" as used herein if a nucleic acid can be obtained through direct cloning from wild-type sequences obtained from wild-type viruses, while they can, for instance, also be obtained through PCR by using different pieces of DNA as a template. This means also that such sequences may be in the wild-type form as well as in altered form. Another option for reaching the same result is through combining synthetic DNA. It is to be understood that "derived" does not exclusively mean a direct cloning of the wild-type DNA. A person skilled in the art will also be aware of the possibilities of molecular biology to obtain mutant forms of a certain piece of nucleic acid. The terms "functional part, derivative and/or analogue thereof" are to be understood as equivalents of the nucleic acid they are related to. A person skilled in the art will appreciate the fact that certain deletions, swaps, (point) mutations, additions, etc., may still result in a nucleic acid that has a similar function as the original nucleic acid. It is, therefore, to be understood that such alterations that do not significantly alter the functionality of the nucleic acids are within the scope of the invention. If a certain adenoviral vector is derived from a certain adenoviral serotype of choice, it is also to be understood that the final product may be obtained through indirect ways, such as direct cloning and synthesizing certain pieces of genomic DNA, using methodology known in the art. Certain deletions, mutations and other alterations of the genomic content that do not alter the specific aspects of the invention are still considered to be part of the invention. Examples of such alterations are, for instance, deletions in the viral backbone to enable the cloning of larger pieces of heterologous nucleic acids. Examples of such mutations are, for instance, E3 deletions or deletions and/or alterations in the regions coding for the E2 and/or E4 proteins of adenovirus. Such changes applied to the adenoviral backbone are known in the art and often applied, since space is a limiting factor for adenovirus to be packaged; this is a major reason to delete certain parts of the adenoviral genome. Other reasons for altering the E2, E3 and/or E4 regions of the genome may be related to stability or integrity of the adenoviral vector as, for instance, described in international patent applications PCT/NL02/00280, PCT/EP03/50125, PCT/NL02/00281, PCT/EP03/50126 (non published). These applications relate, amongst others, to the use of an E4orf6 gene from a serotype from one subgroup in the backbone of an adenovirus from another subgroup to ensure compatibility between the E4orf6 activity and the E1B-55K activity during replication and packaging in a packaging cell line. They further relate to the use of a proper functioning pIX promoter for obtaining higher pIX expression levels and a more stable recombinant adenoviral vector.

"Replication defective" as used herein means that the viral vectors do not replicate in non-complementing cells. In complementing cells, the functions required for replication and, thus, production of the viral vector, are provided by the complementing cell. The replication-defective viral vectors of the invention do not harbor all elements enabling replication in a host cell other than a complementing cell.

"Heterologous" as used herein in conjunction with nucleic acids means that the nucleic acid is not found in wild-type versions of the viral vectors in which the heterologous nucleic acid is cloned. For instance, in the case of adenoviruses, the heterologous nucleic acid that is cloned in the replication-defective adenoviral vector, is not an adenoviral nucleic acid.

"Antigenic determinant" as used herein means any antigen derived from a pathogenic source that elicits an immune response in a host towards which the determinant is delivered (administered). Examples of antigenic determinants of *Plasmodium* that can be delivered by using the replication-defective recombinant viruses of the invention are the circumsporozoite protein, the SE36 polypeptide, the merezoite surface protein 119 kDa C-terminal polypeptide (MSP-119), MSP-1, MSP-142, Liver-Stage Antigen 1 or 3 (LSA-1 or -3), or a fragment of any of the aforementioned. In a preferred aspect, the invention relates to the circumsporozoite (CS) protein from *P. falciparum*.

"Codon-optimized" as used herein means that the nucleic acid content has been altered to reach sufficiently high expression levels of the protein of interest in a host of interest to which the gene encoding the protein is delivered. "Sufficiently high expression levels" in this context means that the protein levels should be high enough to elicit an immune response in the host in order to give protection to a malaria-inducing parasite that may enter the treated host before or after treatment. It is known in the art that some vaccines give an immune response in humans, through which approximately 60% of the vaccinated individuals are protected against illnesses induced by subsequent challenges with the pathogen (e.g., sporozoites). Therefore, the expression levels are considered to be sufficient if 60% or more of the treated individuals are protected against subsequent infections. It is believed that with the combinations of adenoviral aspects that can be applied and the choice of antigen as disclosed herein, such percentages may be reached. Preferably, 85% of the individuals are protected, while it is most preferred to have protection to a subsequent challenge in more than 90% of the vaccinated hosts. The nucleic acids disclosed in the invention are codon optimized for expression in humans. According to Narum et al. (2001), the content of adenine plus thymine (A+T) in DNA of *Homo sapiens* is approximately 59%, as compared to the percentage cytosine plus guanine (C+G). The adenine plus thymine content in *P. falciparum* is approximately 80%. The adenine plus thymine content in the CS gene of *P. falciparum* is approximately 87%. To obtain sufficient protection, it is believed to be necessary to improve production levels in the host. One way to achieve this is to optimize codon usage by altering the nucleic acid content of the antigenic determinant in the viral-based vector, without altering the amino acid molecule thereof. For this, the replication-defective recombinant viral vectors as described herein have an adenine plus thymine content in the heterologous nucleic acids of the invention of less than 87%, preferably less than 80%, and more preferably less than or equal to approximately 59%. Based on codon usage in humans and the amino acid content of the CS genes of *P. falciparum* and yoelii, the percentages of the codon-optimized genes were even lower, reaching approximately 45% for the amino acid content as disclosed herein. Therefore, as far as the CS genes are concerned, it is preferred to have an adenine plus thymine content of approximately 45%. It is to be understood that if a species other than humans is to be treated, which may have a different adenine plus thymine concentration (less or more than 59%), and/or a different codon usage, that the genes encoding the CS proteins of the invention may be adjusted to fit the required content and give rise to suitable expression levels for that particular host. Of course, it cannot be excluded either that slight changes in content may result in slight expression level changes in different geographical areas around the world. It is also to be understood that with slight changes in the number of repeats included in the amino acid molecule of the proteins, that percentages may differ accordingly. All these adjusted contents are part hereof.

The invention is further described with the aid of the following illustrative Examples.

EXAMPLES

Example 1

Assembly of the *Plasmodium falciparum* Circumsporozoite Synthetic Gene

Comparative studies conducted with DNA vaccines based on native and codon-optimized genes encoding merozoite proteins of *P. falciparum* have indicated a direct correlation with expression levels and immunogenicity (Narum et al. 2001). A new sequence of the gene encoding the *Plasmodium falciparum* circumsporozoite (CS) protein was designed. Studies on populations of malaria parasites obtained from widely separated geographical regions have revealed the presence of CS sequence polymorphism. The new *P. falciparum* CS sequence was assembled by alignment of the different available protein sequences present in the GeneBank database (listed in Table I). First, all the different sequences were placed in order of subgroups based on global location or by lab strain where the isolates originated. All CS complete or partial sequences were used in order to identify variation between the different geographical areas and identified lab strains. The final amino acid consensus sequence determined was thoroughly examined. The inventors of the invention subsequently adjusted this consensus sequence to have a new CS gene synthesized (FIG. 1). The novel amino acid molecule is shown in FIG. 1A. The new CS protein harbors the aspects listed below (from N-terminus to C-terminus):

The N-terminal signal sequence, which would direct the protein to the endoplasmic reticulum, is left unchanged.

The HLA-binding peptide amino acid (31-40), as well as region 1 (predominant B-cell epitope) are conserved; therefore, these sequences are left unchanged.

A number of repeats: there are 14-41 NANP (SEQ ID NO:10) repeats in the different isolates and 4 NVDP (SEQ ID NO:11) repeats. It was chosen to incorporate 27 NANP repeats, a cluster of 3 NVDP repeats, and one separate NVDP repeat.

The ENANANNAVKN (SEQ ID NO:12) sequence directly downstream of the repeats mentioned above was found to be reasonably conserved between strains.

The Th2R region and the immunodominant CD8 epitope (Lockyer et al. 1989; Zevering et al. 1994): a single consensus sequence that differs in some respects from that of the known and frequently used lab strain 3D7 sequence was determined. This sequence is sometimes referred to as the "universal epitope" in literature (Nardin et al. 2001).

The region 2, overlapping with the Th2R region, remained conserved.

The TH3R region, which is considered to be a less important CD8 epitope, is used in the form of a consensus sequence, since only point mutations were found.

The C-terminal 28 amino acids, which constitute a GPI signal anchor sequence that is inefficient in mammalian cells (Moran and Caras, 1994) and not hydrophobic by itself, serve as a stable membrane anchor. The gene was constructed such that the whole sequence can be removed, but also leaving open the possibility of remaining present. This allows a comparison of the antigenicity of adenovirus vectors carrying a full-length CS versus those expressing the protein deleted in the GPI signal anchor sequence. In fact, it has been described that removal of the GPI signal sequence from a CS DNA vaccine enhanced induction on immune response against malaria infection in rodents (Scheiblhofer et al. 2001).

Substitution S to A at position 373: this amino acid substitution was introduced to eliminate a potential glycosylation site recognized by mammalian cells.

Since the malaria parasite residue usage (87% A and T) is significantly different from that of the *Homo sapiens*, the gene encoding the newly designed CS protein was codon optimized in order to improve its expression in mammalian cells, taking care of the following aspects to avoid cis-acting sequences: no premature poly(A) sites and internal TATA boxes should be present; Chi-sites, ribosomal entry sites and AT-rich sequence clusters should be avoided; no (cryptic) splice-acceptor and -donor sites should be present; repetitive sequence stretches should be avoided as much as possible; and GC-rich sequences should also be avoided. The final codon-optimized gene is shown in FIG. 1B.

The newly designed CS consensus sequence was synthesized and cloned into pCR-script (Stratagene) by GeneArt (Regensburg, Germany), using methodology known to persons skilled in the art of synthetic DNA generation, giving rise to a clone named 02-148 (pCR-script.Pf) (SEQ ID NO:1).

Next to this synthetic clone, another synthetic gene was generated, wherein a number of mutations were introduced in the 3' end to obtain an amino acid molecule that is identical to the *P. falciparum* CS protein of the 3D7 strain, which is deleted in the last 14 amino acids (FIG. 2). This gene was also codon optimized using the same provisions as described above and subsequently synthesized and cloned into pCR-script (Stratagene) by GeneArt. The clone was named 02-659 (pf-aa-sub) (SEQ ID NO:4).

Example 2

Codon Optimization of the Circumsporozoite Gene of the Rodent-Specific Malaria Parasite *Plasmodium yoelii*

Malaria species that have been adapted to robust rodent models, such as *P. berghei* and *P. yoelii*, have been powerful tools for identification and testing of malaria candidate vaccines. Since infectivity of *P. yoelii* sporozoites resembles that of *P. falciparum*, it was decided to make use of the *P. yoelii* model for exemplification of the capability of Ad35 vectors carrying codon-optimized CS proteins to provide sterile immunity and, therefore, protection against malaria infection. The *P. yoelii* CS gene, encoding for residues 1-356 as previously described (Rodrigues et al. 1997), was codon optimized using the same provisions as described above and synthesized by GeneArt (GmbH-Regensburg, Germany). The sequence of the codon-optimized *P. yoelii* CS gene (plasmid 02-149) is depicted in FIG. 3.

Example 3

Generation of Recombinant Adenoviral Vectors Based on Ad5

RCA-free recombinant adenoviruses can be generated very efficiently using adapter plasmids, such as pAdApt, and adenovirus plasmid backbones, such as pWE/Ad.AflIIrITRsp. Methods and tools have been described extensively elsewhere (WO 97/00326, WO 99/55132, WO 99/64582, WO 00/70071, and WO 00/03029). Generally, the adapter plasmid containing the transgene of interest in the desired expression cassette is digested with suitable enzymes to free the recombinant adenovirus sequences from the plasmid vector backbone. Similarly, the adenoviral complementation plasmid pWE/Ad.AflII-rITRsp is digested with suitable enzymes to free the adenovirus sequences from the vector plasmid DNA.

The cloning of the gene encoding the CS protein from *P. yoelii* parasite into pIPspAdapt1 was performed as follows. Plasmid 02-149 (GeneArt, see above) containing the codon-optimized CS gene was digested with HindIII and BamHI restriction enzymes. The 1.1 Kb fragment corresponding to the *P. yoelii* CS gene was isolated from agarose gel and ligated to HindIII and BamHI-digested pIPspAdapt1 vector (described in WO 99/64582). The resulting plasmid was named pAdapt.CS.Pyoel and contains the CS gene under the transcriptional control of full-length human immediate-early (1E) cytomegalovirus (CMV) promoter and a downstream SV40 poly(A) signal.

The cloning of the gene encoding the full-length CS protein from *P. falciparum* parasite into pIPspAdapt1 was performed as follows. Plasmid 02-148 pCR-script.Pf (see above) containing the codon-optimized CS gene was digested with HindIII and BamHI restriction enzymes. The 1.2 kb fragment corresponding to the CS gene was isolated from agarose gel and ligated to HindIII and BamHI-digested pIPspAdapt1 vector. The resulting plasmid was named pAdapt.CS.Pfalc and contains the CS gene under the transcriptional control of full-length human immediate-early (1E) cytomegalovirus (CMV) promoter and the downstream SV40 poly(A) signal.

The cloning of the gene encoding the CS *P. falciparum* protein minus the GPI anchor sequence, thus with the deletion of the last 28 amino acids, into pIPspAdapt1 was performed as follows. A 1.1 kb PCR fragment was amplified using plasmid 02-148 as template, with the primers Forw.Falc (5'-CCA AGC TTG CCA CCA TGA TGA GG-3') (SEQ ID NO:13) and Rev. Falc.CS-28 (5'-CCG GAT CCT CAG CAG ATC TTC TTC TCG-3') (SEQ ID NO:14). Primers were synthesized by Invitrogen. For the PCR, the enzyme Pwo DNA polymerase (Inno-train Diagnostic) was used, while the following program was applied: one cycle of 5 minutes at 94° C., 1 minute at 50° C., 2 minutes 30 seconds at 72° C.; five cycles of 1 minute at 94° C., 1 minute at 50° C., 2 minutes 50 seconds at 72° C.; twenty cycles of 1 minute at 94° C., 1 minute at 54° C., 2 minutes 50 seconds at 72° C.; and one cycle of 1 minute at 94° C., 1 minute at 54° C., followed by 10 minutes at 72° C. The amplified PCR product was digested with the restriction enzymes HindIII and BamHI and then cloned into pIPspAdapt1 which was also digested with HindIII and BamHI. The resulting plasmid was designated pAdapt.CS.Pfalc(−28) and contains the CS gene under the transcriptional control of full-length human immediate-early (1E) cytomegalovirus (CMV) promoter and the downstream SV40 poly(A) signal.

The cloning of the gene encoding the CS *P. falciparum* protein minus the GPI anchor, thus with the deletion of the last 14 amino acids, into pIPspAdapt1 was performed as follows. A 1.1 kb PCR fragment was amplified using plasmid 02-148 as template, with the primers Forw.Falc (SEQ ID NO:13) and Rev.Falc. CS-14 (5'-CCG GAT CCT CAG CTG TTC ACC ACG TTG-3') (SEQ ID NO:15). Primers were synthesized by Invitrogen. For the PCR, the enzyme Pwo DNA polymerase (Inno-train Diagnostic) was used, while the following program was applied: one cycle of 5 minutes at 94° C., 1 minute at 50° C., 2 minutes 30 seconds at 72° C.; five cycles of 1 minute at 94° C., 1 minute at 50° C., 2 minutes 50 seconds at 72° C.; twenty cycles of 1 minute at 94° C., 1 minute at 54° C., 2 minutes 50 seconds at 72° C.; and one cycle of 1 minute at 94° C., 1 minute at 54° C., followed by 10 minutes at 72° C. The amplified PCR product was digested with the restriction enzymes HindIII and BamHI and then cloned into pIPspAdapt1 also digested with HindIII and BamHI. The resulting plasmid was designated pAdapt.CS.Pfalc(−14) and contains the CS gene under the transcriptional control of full-length human immediate-early (1E) cytomegalovirus (CMV) promoter and the downstream SV40 poly (A) signal.

The cloning of the gene encoding the CS *P. falciparum* protein minus the GPI anchor, displaying a C-terminal sequence as in the 3D7 strain, into pIPspAdapt1 is performed as follows. Plasmid 02-659 pf-aa-sub (see above) containing the codon-optimized CS gene is digested with HindIII and BamHI restriction enzymes. The 1.1 kb fragment corresponding to the CS gene is ligated to HindIII and BamHI-digested pIPspAdapt1 vector. The resulting plasmid is designated pAdapt.CS.Pfalc (pf-aa-sub) and contains the CS gene under the transcriptional control of full-length human immediate-early (1E) cytomegalovirus (CMV) promoter and the downstream SV40 poly(A) signal.

The generation of the recombinant virus named Ad5ΔE3.CS.Pyoel was performed as follows. pAdapt.CS.Pyoel was digested by PacI restriction enzyme to release the left-end portion of the Ad genome. Plasmid pWE/Ad.AflII-rITRsp containing the remaining right-end part of the Ad genome has a deletion of 1878 bp in the E3 region (XbaI deletion). This construct was also digested with PacI. pAdapt.CS.Pyoel was separately transfected with PacI-digested pWE.Ad.AflII-rITRsp into PER-E1B55K producer cells (cells have been described in WO 02/40665) using lipofectamine transfection reagent (Invitrogen) using methods known in the art and as described in WO 00/70071. Homologous recombination between overlapping sequences led to generation of the recombinant virus named Ad5ΔE3.CS.Pyoel. It is to be understood that Ad5-based vectors can also be produced on the aforementioned PER.C6® producer cells, which cells are represented by the cells deposited under ECACC no. 96022940 (see above). The adenoviral vector, in crude lysates, resulting from this transfection was plaque purified using methods known to persons skilled in the art. Single plaques were analyzed for the presence of the CS transgene and amplified for large-scale production in triple-layer flasks (3×175 $cm^2$/flask). Upon amplification, cells are harvested at full CPE and the virus is purified by a two-step Cesium Chloride (CsCl) purification procedure as routinely done by those skilled in the art and generally as described in WO 02/40665.

The generation of the recombinant virus named Ad5ΔE3.CS.Pfalc was performed as follows. pAdapt.CS.Pfalc was digested by PacI restriction enzyme to release the left-end portion of the Ad genome. Plasmid pWE/Ad.AflII-rITRsp containing the remaining right-end part of the Ad genome has a deletion of 1878 bp in the E3 region (XbaI deletion). This construct was also digested with PacI. pAdapt.CS.Pfalc was transfected with PacI-digested pWE.Ad.AflII-rITRsp into PER-E1B55K producer cells using lipofectamine transfection reagent. Homologous recombination between overlapping sequences led to generation of the recombinant virus named Ad5ΔE3.CS.Pfalc. The adenoviral vector in crude lysates resulting from this transfection was plaque purified using methods known to persons skilled in the art. Single plaques were analyzed for the presence of the CS transgene and amplified for large-scale production in triple-layer flasks (3×175 cm²/flask). Cells were harvested at full CPE and the virus was purified by a two-step CsCl purification procedure as routinely done by those skilled in the art and generally as described in WO 02/40665.

The generation of the recombinant viruses named Ad5ΔE3.CS.Pfalc(−28) and Ad5ΔE3.CS.Pfalc(−14) was performed as follows. pAdapt.CS.Pfalc(−28) and pAdapt.CS.Pfalc(−14) were separately digested by PacI restriction enzyme to release the left-end portion of the Ad genome. Plasmid pWE/Ad.AflII-rITRsp containing the remaining right-end part of the Ad genome has a deletion of 1878 bp in the E3 region (XbaI deletion). This construct was also digested with PacI. pAdapt.CS.Pfalc(−28) and pAdapt.CS.Pfalc(−14) were separately transfected with PacI-digested pWE.Ad.AflII-rITRsp into PER-E1B55K producer cells using lipofectamine transfection reagent. Homologous recombination between overlapping sequences led to generation of recombinant viruses named, respectively, Ad5ΔE3.CS.Pfalc(−28) and Ad5ΔE3.CS.Pfalc(−14). Adenoviral vectors in crude lysates resulting from these transfections are plaque purified using methods known to persons skilled in the art. Single plaques are analyzed for the presence of the CS transgene and amplified for large-scale production in triple-layer flasks (3×175 cm²/flask). Cells are harvested at full CPE and the virus is purified by a two-step CsCl purification procedure as routinely done by those skilled in the art and generally as described in WO 02/40665.

The generation of the recombinant virus named Ad5ΔE3.CS.Pfalc(pf-aa-sub) is performed as follows. pAdapt.CS.Pfalc(pf-aa-sub) is digested by PacI restriction enzyme to release the left-end portion of the Ad genome. Plasmid pWE/Ad.AflII-rITRsp containing the remaining right-end part of the Ad genome is also digested with PacI. pAdapt.CS.Pfalc(pf-aa-sub) is transfected with PacI-digested pWE.Ad.AflII-rITRspΔE3 into PER.C6® or PER-E1B55K producer cells using lipofectamine transfection reagent, or by other means such as electroporation or other transfection methods known to persons skilled in the art. Homologous recombination between overlapping sequences leads to generation of the recombinant virus named Ad5ΔE3.CS.Pfalc (pf-aa-sub). The adenoviral vector, in crude lysates, resulting from this transfection is plaque purified using methods known to persons skilled in the art. Single plaques are analyzed for the presence of the CS transgene and amplified for large-scale production in triple-layer flasks (3×175 cm²/flask). C The 1.2 kb fragment corresponding to the CS gene was isolated over agarose gel and ligated to the HindIII and BamHI-digested pAdapt535 vector. The resulting plasmid was named pAdapt535-CS.Pfalc and contains the CS gene under the transcriptional control of the full-length human CMV promoter and the downstream SV40 poly(A) signal.

The cloning of the gene encoding the CS *P. falciparum* protein minus the GPI anchor sequence, thus with the deletion of the last 28 amino acids, into pAdapt535 is performed as follows. The 1.1 kb PCR fragment obtained as described above using primers Forw.Falc and Rev. Falc.CS-28 is digested with the restriction enzymes HindIII and BamHI and then cloned into pAdapt535 vector also digested with HindIII and BamHI. The resulting plasmid is designated pAdapt535.CS.Pfalc(−28) and contains the CS gene under the transcriptional control of the full-length human CMV promoter and the downstream SV40 poly(A) signal.

The cloning of the gene encoding the CS *P. falciparum* protein minus the GPI anchor sequence, now with the deletion of the last 14 amino acids, into pAdapt535 is performed as follows. The 1.1 kb PCR fragment obtained as described above using primers Forw.Falc and Rev. Falc.CS-14 is digested with the restriction enzymes HindIII and BamHI and then cloned into pAdapt535 vector also digested with HindIII and BamHI. The resulting plasmid is designated pAdapt535.CS.Pfalc(−14) and contains the CS gene under the transcriptional control of the full-length human CMV promoter and the downstream SV40 poly(A) signal.

The cloning of the gene encoding the CS *P. falciparum* protein minus the GPI anchor sequence, displaying a C-terminus sequence as in the 3D7 strain, into pAdapt535 is performed as follows. Plasmid 02-659 pf-aa-sub (see above) containing the codon-optimized CS gene is digested with HindIII and BamHI restriction enzymes. The 1.1 kb fragment corresponding to the CS gene is ligated to HindIII and BamHI-digested pAdapt535 vector. The resulting plasmid is designated pAdapt535.CS.Pfalc(pf-aa-sub) and contains the CS gene under the transcriptional control of the full-length human CMV promoter and the downstream SV40 poly(A) signal.

The generation of the recombinant virus named Ad35ΔE3.CS.Pyoel was performed as follows. pAdapt535.CS.Pyoel was digested by PacI restriction enzyme to release the left-end portion of the Ad genome. Plasmid pWE.Ad35.pIX-rITRΔE3 containing the remaining right-end part of the Ad genome with a deletion of 2673 bp in the E3 region is digested with NotI. pAdapt535.CS.Pyoel was transfected with NotI-digested pWE.Ad35.pIX-rITRΔE3 into PER-E1B55K producer cells using lipofectamine transfection reagent. The generation of the cell line PER-E1B55K has been described in detail in WO 02/40665. In short, this publication describes that PER.C6® cells were stably transfected with ScaI linearized pIG35-55K DNA, carrying the E1B-55K gene of adenovirus serotype 35, after which a selection procedure with G418 yielded in 196 picked colonies. Further culturing of a limited number of well-growing colonies resulted in stable cell lines that, upon numerous subcultures, stably expressed the Ad35 E1B-55K gene and supported the growth of recombinant Ad35 viruses, while the original PER.C6® cell were very inefficient in supporting this.

Homologous recombination between overlapping sequences led to generation of the recombinant virus named Ad35ΔE3.CS.Pyoel. The adenoviral vector, in crude lysates, resulting from this transfection was plaque purified using methods known to persons skilled in the art. Single plaques were analyzed for the presence of the CS transgene and amplified for large-scale production in triple-layer flasks ($3\times175$ $cm^2$/flask). Upon amplification, cells were harvested at full CPE and the virus was purified by a two-step CsCl purification procedure as routinely done by those skilled in the art and generally as described in WO 02/40665.

The generation of the recombinant virus named Ad35ΔE3.CS.Pfalc was performed as follows. pAdapt535.CS.Pfalc was digested by PacI restriction enzyme to release the left-end portion of the Ad genome. Plasmid pWE.Ad35.pIX-rITRΔE3 containing the remaining right-end part of the Ad genome with a deletion of 2673 bp in the E3 region was digested with NotI. pAdapt535.CS.Pfalc was transfected with NotI-digested pWE.Ad35.pIX-rITRΔE3 into PER-E1B55K producer cells using lipofectamine transfection reagent. Homologous recombination between overlapping sequences led to generation of the recombinant virus named Ad35ΔE3.CS.Pfalc. The adenoviral vector in crude lysates resulting from this transfection was plaque purified using methods known to persons skilled in the art. Single plaques were analyzed for the presence of the CS transgene and amplified for large-scale production in triple-layer flasks ($3\times175$ $cm^2$/flask). Upon amplification, cells were harvested at full CPE and the virus was purified by a two-step CsCl purification procedure as routinely done by those skilled in the art and generally as described in WO 02/40665.

The generation of the recombinant viruses named Ad35ΔE3.CS.Pfalc(−28) and Ad35ΔE3.CS.Pfalc(−14) is performed as follows. pAdapt535.CS.Pfalc(−28) and pAdapt535.CS.Pfalc(−14) were separately digested by PacI restriction enzyme to release the left-end portion of the Ad genome. Plasmid pWE.Ad35.pIX-rITRΔE3 containing the remaining right-end part of the Ad genome is digested with NotI. pAdapt535.CS.Pfalc(−28) and pAdapt535.CS.Pfalc(−14) are separately transfected with NotI-digested pWE.Ad35.pIX-rITRΔE3 into PER-E1B55K producer. Homologous recombination between overlapping sequences leads to generation of recombinant viruses named, respectively, Ad35ΔE3.CS.Pfalc(−28) and Ad35ΔE3.CS.Pfalc(−14). Adenoviral vectors in crude lysates resulting from these transfections are plaque purified using methods known to persons skilled in the art. Single plaques are analyzed for the presence of the CS transgene and amplified for large-scale production in triple-layer flasks ($3\times175$ $cm^2$/flask). Cells are harvested at full CPE and the virus is purified by a two-step CsCl purification procedure as routinely done by those skilled in the art and generally as described in WO 02/40665.

The generation of the recombinant virus named Ad35ΔE3.CS.Pfalc(pf-aa-sub) is performed as follows. pAdapt535.CS.Pfalc(pf-aa-sub) is digested by PacI restriction enzyme to release the left-end portion of the Ad genome. Plasmid pWE.Ad35.pIX-rITRΔE3 containing the remaining right-end part of the Ad genome is digested with NotI. pAdapt535.CS.Pfalc(pf-aa-sub) is transfected with NotI-digested pWE.Ad35.pIX-rITRΔE3 into PER-E1B55K producer cells using lipofectamine transfection reagent (Invitrogen) using methods known in the art and as described in WO 00/70071 or by electroporation or other transfection methods known to those skilled in the art. Homologous recombination between overlapping sequences leads to generation of the recombinant virus named Ad35ΔE3.CS.Pfalc(pf-aa-sub). The adenoviral vector in crude lysates resulting from this transfection is plaque purified using methods known to persons skilled in the art. Single plaques are analyzed for the presence of the CS transgene and amplified for large-scale production in triple-layer flasks ($3\times175$ $cm^2$/flask). Cells are harvested at full CPE and the virus is purified by a two-step CsCl purification procedure as routinely done by those skilled in the art and generally as described in WO 02/40665.

Example 5

Figure 4B:
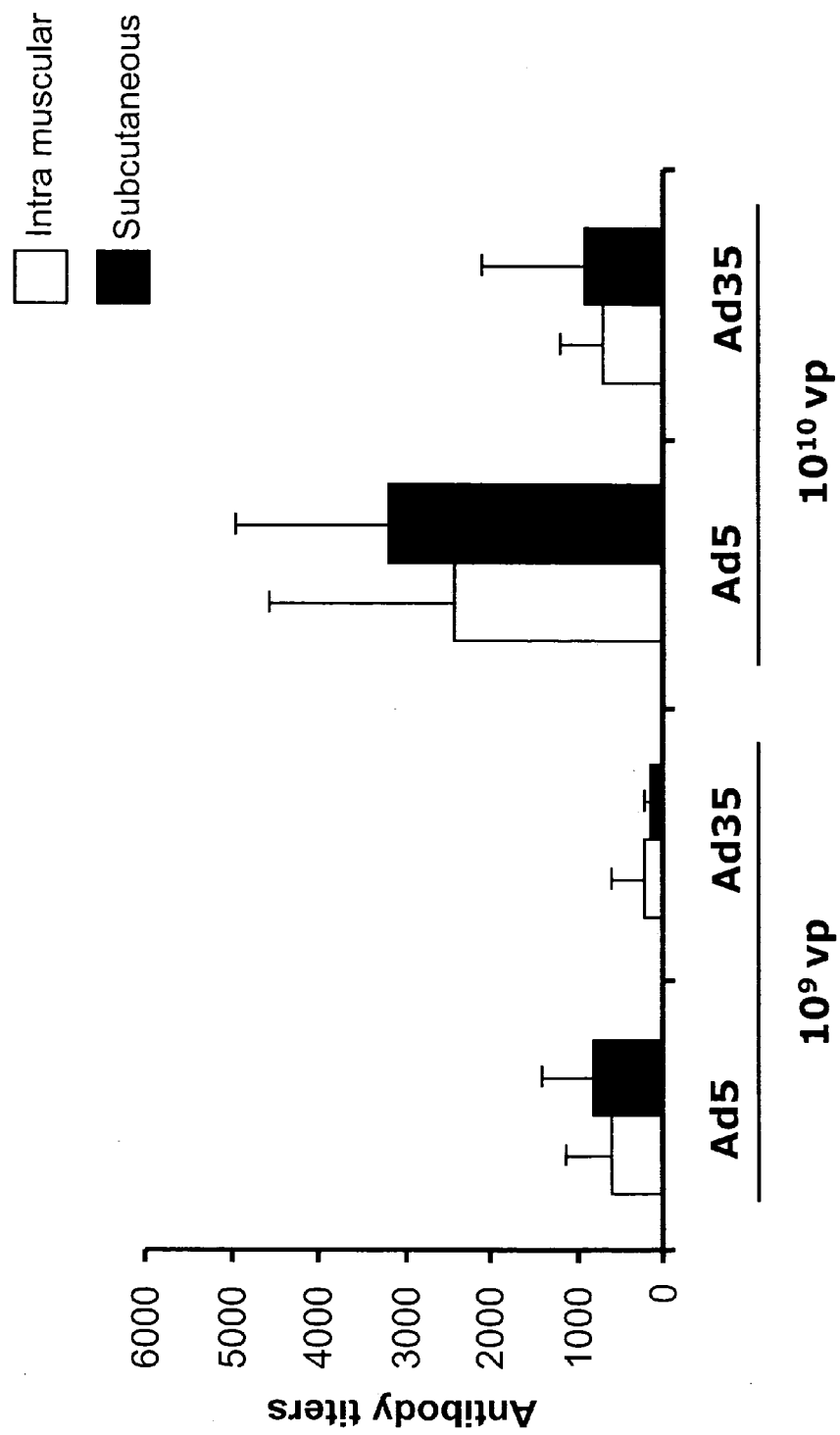
Figure 5A:
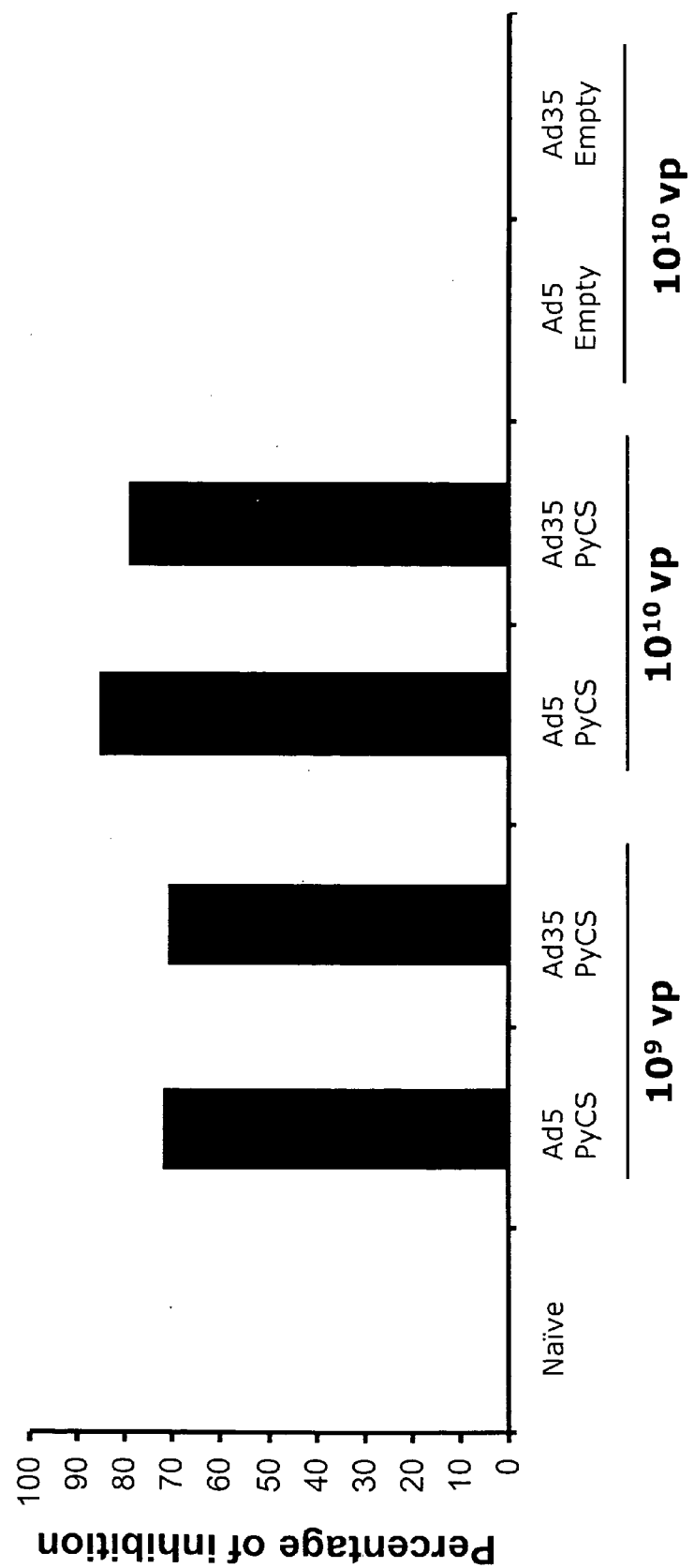
Figure 5B:
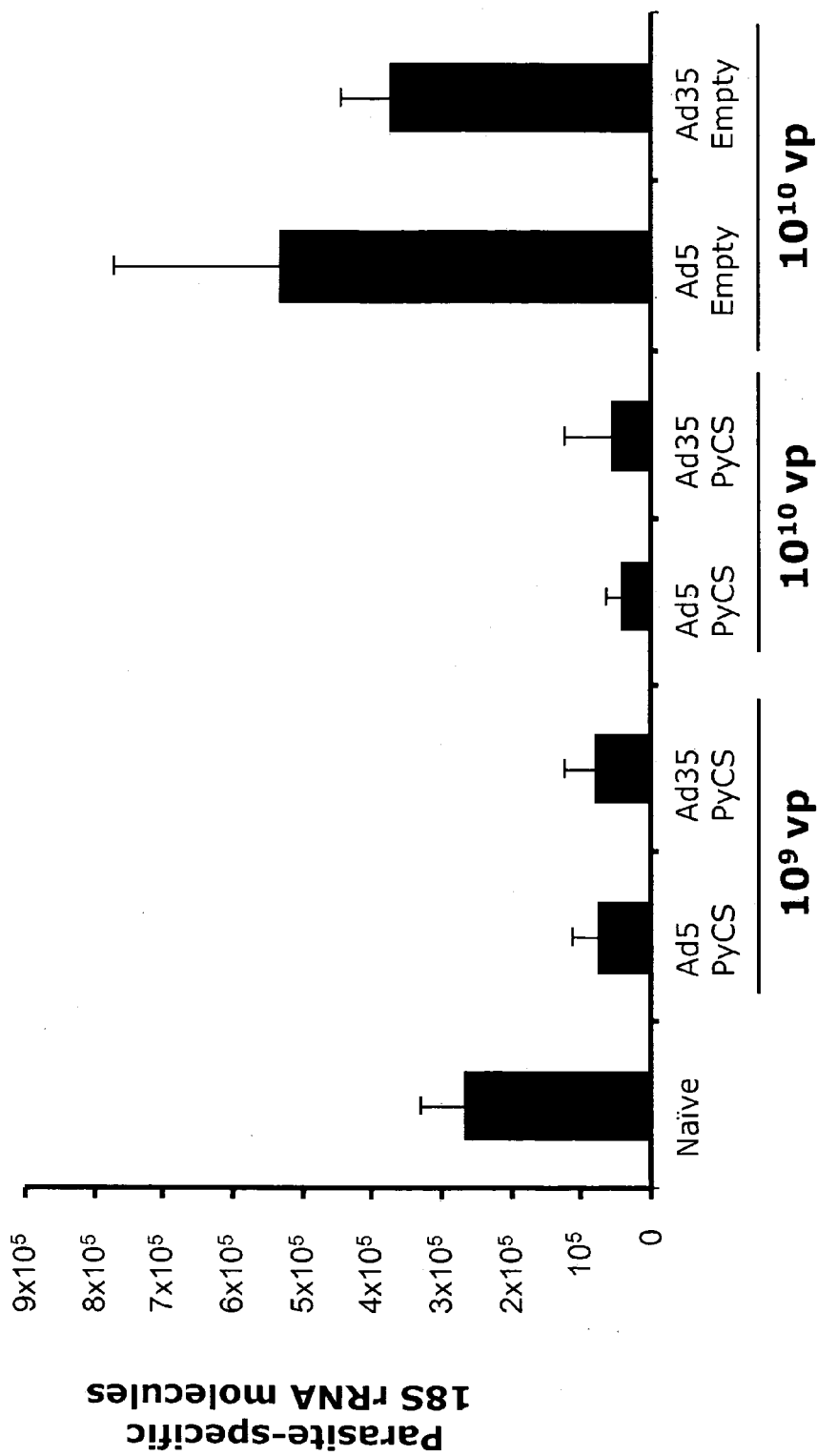

Inducing Protection Against *P. yoelii* Malaria Infection Using Recombinant Adenoviral-Based Vaccines In Vivo Ad5-based vectors genetically engineered to express the CS antigen of the rodent malaria *P. yoelii* have been shown capable to induce complete protection against *P. yoelii* infection (Rodrigues et al. 1997). A side-by-side comparison between Ad5 and Ad35 vectors carrying the codon-optimized *P. yoelii* CS gene was designed to investigate the immune response that is induced and to investigate their ability in raising protection against *P. yoelii* parasite infection in mice. The study enrolled Balb/C mice that were immunized by intra-muscular or subcutaneous injection of $10^8$-$10^{10}$ viral particles (vp) of Ad5ΔE3- or Ad35ΔE3-based viral vectors (as described above) carrying either the *P. yoelii* CS gene (Ad5ΔE3-CS.Pyoel and Ad35ΔE3-CS.Pyoel) or no transgene (Ad5ΔE3-empty and Ad35ΔE3-empty). FIG. 4 shows the results of the experiments wherein the administration route was compared using both vectors. The number of IFN-γ-secreting cells in a population of $10^6$ splenocytes was determined (FIG. 4A), as well as the antibody titers in the serum (FIG. 4B). The experiments were performed on mice that were sacrificed two weeks after injection with the recombinant adenoviruses. Each of the bars represents the average of five mice. If mice were not sacrificed, they were used for a challenge with live sporozoites, after which the rate of protection was determined (FIGS. 5A and 5B). Each of these bars represents the average of five mice. The experiments on humoral and cellular immune responses are performed with immunological assays well known to persons skilled in the art and as described, for instance, by Bruña-Romero et al. (2001a). The immunization, challenge and read out are scheduled in Tables II and III. Antibodies titers against sporozoites can be determined by an indirect immunofluorescence assay or with an ELISA. FIG. 4B shows the results as calculated with an ELISA. Cellular immune responses were determined by ex vivo ELISPOT assay measuring the relative number of CS-specific, IFN-γ-secreting, CD8+ and CD4+ T-cells. Protection against malaria infection was monitored by determining the levels of parasite inhibition in the livers of immunized mice through reverse transcriptase PCR quantification of *P. yoelii* ribosomal RNA copies.

The immunization with Ad5- and Ad35-based vectors was performed as follows. Aliquots of recombinant adenoviruses that were stored at −70° C. were gradually thawed on ice and diluted to 100 μl in the desired concentration in PBS with 1% heat-inactivated Normal Mouse Serum. Subsequently, the samples were sonicated for five seconds. Subcutaneous administration was performed at both sides of the tail base with a volume of 50 μl at each side. Intra muscular administration was performed in both thighs with a volume of 50 μl at each thigh.

The Indirect Immunofluorescence Assay ("IFA") is performed according to Bruña-Romero et al. (2001a). First, infected mosquitoes are generated by initially having a native mouse infected with an infected mosquito by having the mouse bitten at three different sites. Blood is removed from the mouse after eight days when parasitemia is 4-8% and diluted to 1%. Then, other naïve mice are injected i.p. with the diluted blood sample. After three days, the blood is taken which serves as a blood meal for starved mosquitoes. These are fed for two days. After 14 days, *P. yoelii* sporozoites are isolated from the blood-fed mosquitoes by anesthetizing infected mosquitoes on ice and subsequently saturating them in 70% ethanol. Then, the mosquitoes are transferred to PBS pH 7.4 and the salivary glands are dissected. These are subsequently grinded on ice and the sporozoites are separated from the debris by centrifugation. Using this method, approximately 35,000 *P. yoelii* sporozoites can be obtained from one mosquito. Then, glass slides in a 12-multi-well plate are coated with approximately 10,000 *P. yoelii* sporozoites, each in Dulbecco's Modified Eagle's Medium (DMEM) plus 10% Fetal Bovine Serum by air drying. A range of dilutions of sera of the vaccinated mice (in a volume of 10 μl in PBS plus 5% FBS) is subsequently incubated with the air-dried sporozoites for 30 minutes at room temperature in a moistures environment. Then, the slides are aspirated, washed twice with PBS and 10 μl of a 30-fold diluted FITC-conjugated Goat-anti-Mouse antibody (Kirkegaard & Perry Laboratories, USA, catalogue no. 02-18-06) is added and incubated for 30 minutes at room temperature. Wells were again aspirated and washed twice. For counter-staining, a solution of 100 μg/ml Ethidium Bromide is incubated for ten minutes, after which the aspiration step is repeated and the wells are washed with water. Slides are mounted using permount containing phenylenediamine/anti-fade. The anti-sporozoite antibody titers are determined as the highest serum dilution-producing fluorescence. For the determination of antibody titers, one can also use an ELISA. For this, ELISA plates (IMMULON® II, Dynatech) were coated with 2 μg/ml antigen in PBS by adding 100 μl per well of this solution and leaving it overnight at 4° C. The antigen that was used is a 3×6 amino acid repeat of the *P. yoelii* CS protein: QGPGAPQGPGAPQGPGAP (SEQ ID NO:19). The plates were subsequently washed three times with washing buffer (1×PBS, 0.05% TWEEN™), and 200 μl blocking buffer (10% FCS in washing solution) was added per well. Plates were incubated for one to two hours at room temperature. Then, plates were washed three times again with washing buffer including 5% FCS. Dilutions of the sera were made as follows: 50 μl washing buffer plus 5% FCS was added to wells 2-12. Then 100 μl washing buffer plus 5% FCS is added to the first well and 1:2 serial dilutions are made by transferring 50 μl from well 1 to 2, then from 2 to 3, etc. Plates are incubated for one hour at room temperature. Then, the plates are washed three times with washing buffer and 100 μl of a 1:2000 diluted peroxidase-labeled Goat anti-Mouse IgG (anti Heavy and Light chain, human absorbed, Kirkegaard & Perry Laboratories, catalogue no. 074-1806) is added per well and incubated. Then, plates are washed with washing buffer three times and once with PBS and then 100 μl ABTS substrate solution (ABTS 1-Component, Kirkegaard & Perry Laboratories, catalogue number 50-66-18) is added to each well. The reaction is terminated by the addition of 50 μl 1% SDS and plates are read at 405 nm in an ELISA reader.

The ELISPOT assay to determine the relative number of CS-specific IFN-γ-secreting CD8+ and CD4+ T-cells in the spleen, and the reverse transcriptase PCR and real-time PCR to quantify the amount of parasite-specific RNA present in the liver of the challenged mice were all performed as described by Bruña-Romero et al. (2001a and 2001b), except for the fact that the number of cycles in the real-time PCR was 45.

While attenuation *P. yoelii* infection in Ad5ΔE3-CS.Pyoel vaccine recipients is predicted (Rodrigues et al. 1997), vaccination with Ad35ΔE3-CS.Pyoel is expected to be superior or at least equally effective.

FIG. 4A shows that with an administration of $10^9$ and $10^{10}$ viral particles per mouse, the Ad35-based vector is at least as effective in inducing a cellular immune response as the Ad5- based vector, if not superior. It can be concluded that with this set-up, there is no dramatic difference in cellular response as indicated by the number of IFN-γ-secreting cells after intramuscular and subcutaneous delivery.

FIG. 4B shows the antibody titers in the same experiment and performed on the same sera using the indirect immunofluorescence experiment outlined above. If compared to the results shown in FIG. 4A, it is clear that at a dose of $10^9$ viral particles, the Ad35-based vector induces a significant cellular immune response but does not give rise to very high titers of anti-sporozoite antibodies. Again, there is not a significant difference between the two routes of administration.

Animals that received different doses of Ad5- and Ad35-based vectors expressing the codon-optimized P. yoelii CS antigen, were subsequently challenged i.v. with $10^5$ sporozoites purified as described above. The results of these experiments are shown in FIGS. 5A and 5B. The percentage of inhibition was calculated as compared to naïve mice that were not immunized.

Mice that were immunized received s.c. $10^9$ or $10^{10}$ viral particles (vp) and were challenged after 14 days with the sporozoites and then sacrificed after 48 hours. Negative controls were empty vectors without antigen and non-immunized mice. Clearly, a high percentage of inhibition is obtained when using the Ad5-based vector as well as with the Ad35-based vector, applying the two doses, while no protection was found in the negative controls (FIG. 5A). Importantly, only a low number of parasite-specific 18S ribosomal RNAs could be determined in the liver of the immunized mice, while the mice that received no adenoviral vector or empty vectors contained large numbers of these RNAs (FIG. 5B). This strongly indicates that the Ad35-based vector, like the Ad5-based vector, can give rise to significant protection against the malaria parasite, even after a single round of immunization.

Example 6

Inducing Immunity Against P. falciparum Malaria Infection Using Recombinant Adenoviral-Based Vaccines In Vivo A side-by-side comparison between Adenovirus serotype 5 (Ad5) and Adenovirus serotype 35 (Ad35) vectors is designed to investigate the ability to induce humoral and cellular immune responses against the CS antigen of the P. falciparum parasite in mice. In addition, immunogenicities of Adenovirus vectors containing full-length and GPI minus CS are compared. This study enrolls B10.BR mice. Animals are immunized by intramuscular injection of $10^8$-$10^{10}$ vp of Ad5ΔE3 or Ad35ΔE3 viral vectors carrying either the full-length CS gene (Ad5ΔE3-CS.Pfalc and Ad35ΔE3-CS.Pfalc) or the GPI-anchor sequence minus CS gene (Ad5ΔE3-CS.Pfalc.(−28)/(−14) and Ad35ΔE3-CS.Pfalc.(−28)/(−14)) or no transgene (Ad5ΔE3-empty and Ad35ΔE3-empty). At two weeks and six to eight weeks post-vaccination, cellular and humoral responses are monitored with immunological assays well known to persons skilled in the art as described above. The immunization, challenge and read out are scheduled in Tables IV and V.

Figure 6:
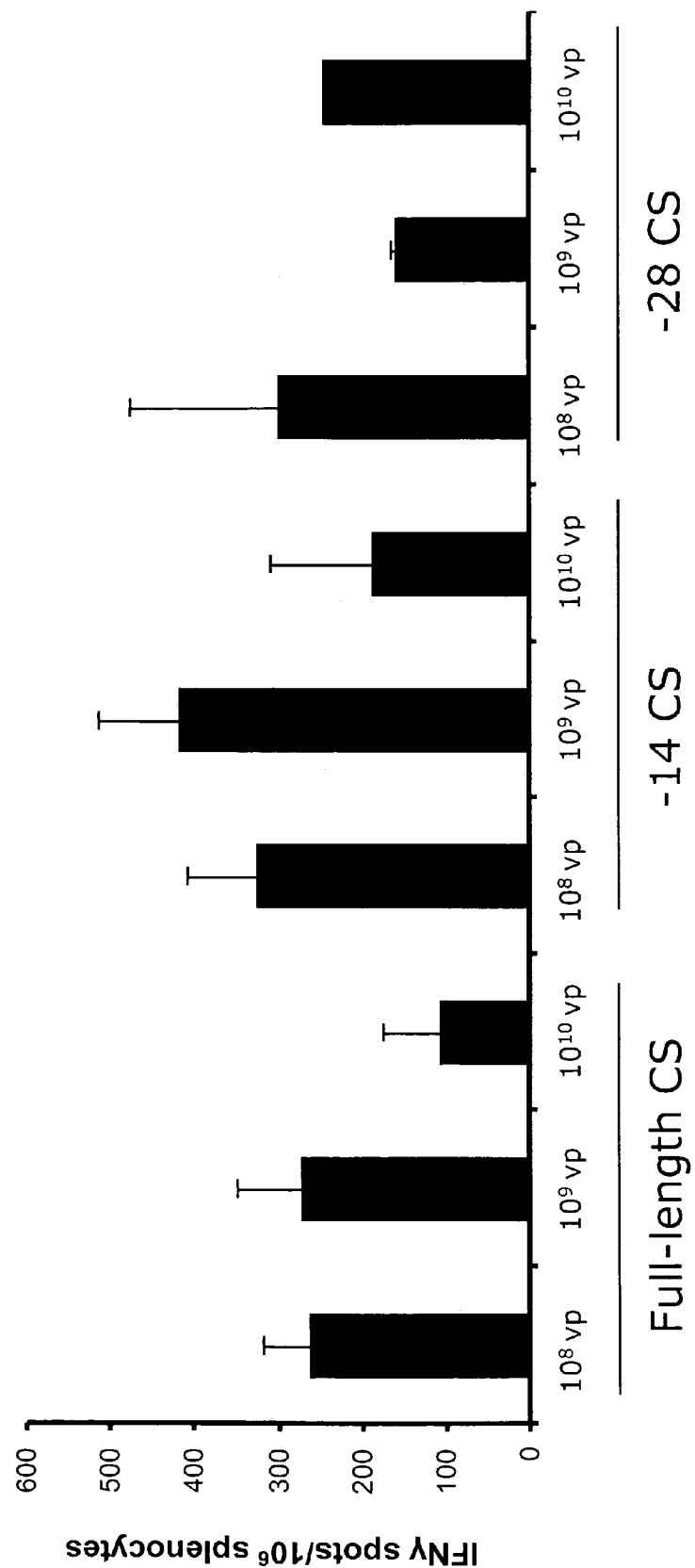

Immunogenicity of the Ad35-based vectors is expected to be superior or at least comparable to the immunogenicity triggered by Ad5-based vectors. FIG. 6 shows the results that were obtained by using the Ad5-based vector containing the full-length gene encoding the P. falciparum CS protein, the gene encoding the protein with the 14 amino acid deletion and the gene encoding the protein with the 28 amino acid deletion. The results indicate that all three (Ad5-based) vectors are able to induce a cellular immune response as measured by the number of CS-specific IFN-γ-secreting cells in a population of splenocytes, determined by the ex vivo ELISPOT assay described above, and generally as in Bruña-Romero et al. (2001a).

Example 7

Inducing a Long-Lasting Protection Against P. yoelii Malaria Infection by Prime-Boost Regimens with Different Adenovirus Serotype-Based Vaccines Recombinant Adenovirus serotype 5 expressing a CS antigen of P. yoelii was shown to elicit protection when used in prime-boost regimen in combination with a recombinant vaccinia virus carrying the same antigen (Bruña-Romero et al. 2001a). An experiment to investigate the capability of prime/boost regimens based on adenovirus vectors carrying codon-optimized CS and derived from two different serotypes to induce long-lasting protection against the P. yoelii CS antigen was designed. This study enrolls Balb/C mice distributed in experimental groups of 12 mice each. Animals are immunized by intramuscular injection of an optimal dose of Ad5ΔE3 or Ad35ΔE3 viral vectors carrying either the P. yoelii CS gene (Ad5ΔE3-CS.Pyoel and Ad35ΔE3-CS.Pyoel) or no transgene (Ad5ΔE3-empty and Ad35ΔE3-empty). One group of animals is primed at week 0 with Ad5ΔE3-CS.Pyoel and boosted at week 8 with Ad35ΔE3-CS.Pyoel. Another group of mice is primed at week 0 with Ad35ΔE3-CS.Pyoel and boosted at week 8 with Ad5ΔE3-CS.Pyoel. Other groups of mice are primed at week 0 with Ad35ΔE3-CS.Pyoel or Ad5ΔE3-CS.Pyoel and boosted at week 8 with the same vector. Finally, a control group of mice is primed at week 0 with Ad5ΔE3-empty and boosted at week 8 with Ad35ΔE3-empty. At week 2 post-boost, six mice of each group are sacrificed to allow evaluation and characterization of humoral and cellular immune responses with immunological assays well known to persons skilled in the art. The remaining six mice from each group are challenged with live sporozoites. The immunization, challenge and read out are scheduled in Table VI. Protection against malaria infection will be monitored and measured using assays well known to people skilled in the art as described above. Vaccine regimens based on Ad35 alone or Ad5/Ad35 combinations are expected to be superior or at least comparable in efficacy as compared to regimens based solely on Ad5.

Example 8

Inducing a Long-Lasting Immunity Against P. falciparum Malaria Infection by Prime-Boost Regimens with Different Adenovirus Serotype-Based Vaccines An experiment to investigate the ability of prime/boost regimens based on adenovirus vectors derived from two different serotypes to induce long-lasting immunity against the P. falciparum CS antigen was designed. The study enrolls B10.BR mice distributed in experimental groups of 24 mice each. Animals are immunized by intramuscular injection of an optimal dose of adenoviral vectors carrying either the full-length CS gene (Ad5ΔE3-CS.Pfalc and Ad35ΔE3-CS.Pfalc) or the GPI-anchor sequence minus CS gene (Ad5ΔE3-CS.Pfalc(−28)/(−14) and Ad35ΔE3-CS.Pfalc(−28)/(−14)) or no transgene (Ad5ΔE3-empty and Ad35ΔE3-empty). One group of animals is primed at week 0 with Ad5ΔE3-CS.Pfalc or Ad5ΔE3-CS.Pfalc(−28)/(−14) and boosted at week 8 with Ad35ΔE3-CS.Pfalc or Ad35ΔE3-CS.Pfalc(−28)/(−14). Another group of mice is primed at week 0 with Ad35ΔE3-CS.Pfalc or Ad35ΔE3-CS.Pfalc(−28)/(−14) and boosted at week 8 with Ad5ΔE3-CS.Pfalc or Ad5ΔE3-CS.Pfalc(−28)/(−14). Another group of mice is primed at week 0 with Ad35ΔE3-CS.Pfalc or Ad35ΔE3-CS.Pfalc(−28)/(−14) and boosted at week 8 with the same vector. Finally, a control group of mice is primed at week 0 with Ad5ΔE3-empty and boosted at week 8 with Ad35ΔE3-empty. At weeks 2 and 6 or 10 or 16 post-boost, six mice are sacrificed at each time point and cellular and humoral responses are monitored with immunological assays well known to persons skilled in the art and as described above. The immunization, challenge and read out are scheduled in Table VII. Vaccine regimens based on Ad35 alone or Ad5/Ad35 combinations are expected to be superior or at least comparable in efficacy as compared to regimens based solely on Ad5.

Example 9

Inducing an Immune Response Against the *P. falciparum* CS Antigen by Prime/Boost Regimens Using Different Adenovirus Serotype-Based Vaccines in Non-Human Primates An example of an experiment useful to investigate the capability of prime/boost regimens based on adenovirus vectors derived from two different serotypes to elicit immunity against the *P. falciparum* CS antigen in non-human primates is described. Moreover, the effect of two different routes of vaccine administration, intramuscular and intradermal, is evaluated.

Rhesus monkeys are vaccinated with adenoviral vectors carrying either the full-length CS gene (Ad5ΔE3-CS.Pfalc or Ad35ΔE3-CS.Pfalc) or the GPI-anchor sequence minus CS gene (Ad5ΔE3-CS.Pfalc(pf-aa-sub) or Ad35ΔE3-CS.Pfalc (pf-aa-sub)). Prime/boost regimens (Ad5 followed by Ad35 or Ad35 followed by Ad5) are compared to generally applied prime/boost regimens (Ad5 followed by Ad5 or Ad35 followed by Ad35). Humoral and cellular immune responses are monitored using immunological assays well known to persons skilled in the art. Serum of immunized monkeys is tested by ELISA assay to determine the nature and magnitude of the antibody response against the repeat region of CS. Cellular immune response is measured by ELISPOT assay to determine the amount of antigen-specific IFN-γ-secreting cells.

TABLE I

Names and Genbank database entry numbers of the
*P. falciparum* circumsporozoite amino acid molecules
used to generate the final consensus sequence.

| Wild-type isolates | Entry numbers | Lab strains | Entry numbers |
|---|---|---|---|
| China | AAG37074 | 3D7 | CAA33421 |
| Thailand | CAB64171 | | CAB38998 |
| | CSP_PLAFT | | CSP_PLAFO |
| | AAA29542-AAA29552 | | NP_473175 |
| | AAA29555-AAA29576 | 7G8 | CSP_PLAFA |
| Brazil | CAB64167 | | C60657 |
| | CAB64190-CAB64197 | | AAA29524 |
| Senegal | CAB64180-CAB64189 | NF54 | AAA29521 |
| Myanmar | CAB64237-CAB64243 | | AAA29527 |
| India | CAB64169 | | S05428 |
| Tanzania | CAB64168 | | CSP_PLAFL |
| | CAB64170 | WELLCOME | A54529 |
| | CAB64172 | | AAA29554 |

TABLE I-continued

Names and Genbank database entry numbers of the
*P. falciparum* circumsporozoite amino acid molecules
used to generate the final consensus sequence.

| Wild-type isolates | Entry numbers | Lab strains | Entry numbers |
|---|---|---|---|
| Gambia | AAF03134-AAF03136 | | CSP_PLAFW |
| | A38869 | | D60657 |
| | B60657 | LE5 | CSP_PLAFL |
| | B38869 | | AAA57043 |
| | H60657 | | B29765 |
| Uganda | CAA27599 | | |
| | CAB64177 | | |
| Liberia | CAB64176 | | |
| Honduras | CAB64174 | | |
| South East Asia | AAA29516-AAA29519 | | |
| | CAB64175 | | |
| | CAB64178 | | |
| | CAB64179 | | |

TABLE II

Immunization, challenge and read-out schedules for mice vaccinations
with Ad5.CS.Pyoel (Ad5-PyCS), vp = viral particles per mouse.

| Immunization schedule | Viral vector | vp | # mice | ELISPOT/ serum | Challenge |
|---|---|---|---|---|---|
| Prime/challenge | Ad5-PyCS | $10^8$ | 12 | 2 weeks (6 mice) | 2 weeks (6 mice) |
| Prime/challenge | Ad5-PyCS | $10^9$ | 12 | 2 weeks (6 mice) | 2 weeks (6 mice) |
| Prime/challenge | Ad5-PyCS | $10^{10}$ | 12 | 2 weeks (6 mice) | 2 weeks (6 mice) |
| Prime/challenge | Ad5-empty | $10^{10}$ | 8 | 2 weeks (4 mice) | 2 weeks (4 mice) |

TABLE III

Immunization, challenge and read-out schedules
for mice vaccinations with Ad35.CS.Pyoel (Ad35-
PyCS), vp = viral particles per mouse.

| Immunization schedule | Viral vector | vp | # mice | ELISPOT/ serum | Challenge |
|---|---|---|---|---|---|
| Prime/challenge | Ad35-PyCS | $10^8$ | 12 | 2 weeks (6 mice) | 2 weeks (6 mice) |
| Prime/challenge | Ad35-PyCS | $10^9$ | 12 | 2 weeks (6 mice) | 2 weeks (6 mice) |
| Prime/challenge | Ad35-PyCS | $10^{10}$ | 12 | 2 weeks (6 mice) | 2 weeks (6 mice) |
| Prime/challenge | Ad35-empty | $10^{10}$ | 8 | 2 weeks (4 mice) | 2 weeks (4 mice) |

TABLE IV

Immunization, challenge and read-out schedules for
mice vaccinations with Ad5.CS.Pfalc (Ad5-PfCS, with
or without anchor), vp = viral particles per mouse.

| Immunization schedule | Viral vector | vp | # mice | ELISPOT/ serum | ELISPOT/ serum |
|---|---|---|---|---|---|
| Prime | Ad5-PfCS | $10^8$ | 12 | 2 weeks (6 mice) | 6-8 weeks (6 mice) |
| Prime | Ad5-PfCS | $10^9$ | 12 | 2 weeks (6 mice) | 6-8 weeks (6 mice) |
| Prime | Ad5-PfCS | $10^{10}$ | 12 | 2 weeks (6 mice) | 6-8 weeks (6 mice) |
| Prime | Ad5-empty | $10^{10}$ | 8 | 2 weeks (4 mice) | 6-8 weeks (4 mice) |

TABLE V

Immunization, challenge and read-out schedules for mice vaccinations with Ad35.CS.Pfalc (Ad35-PfCS, with or without anchor), vp = viral particles per mouse.

| Immunization schedule | Viral vector | vp | # mice | ELISPOT/ serum | ELISPOT/ serum |
|---|---|---|---|---|---|
| Prime | Ad35-PfCS | $10^8$ | 12 | 2 weeks (6 mice) | 6-8 weeks (6 mice) |
| Prime | Ad35-PfCS | $10^9$ | 12 | 2 weeks (6 mice) | 6-8 weeks (6 mice) |
| Prime | Ad35-PfCS | $10^{10}$ | 12 | 2 weeks (6 mice) | 6-8 weeks (6 mice) |
| Prime | Ad35-empty | $10^{10}$ | 8 | 2 weeks (4 mice) | 6-8 weeks (4 mice) |

TABLE VI

Immunization, challenge and read-out schedules for mice in a prime-boost vaccination set-up using Ad5.CS.Pyoel (Ad5-PyCS) and Ad35.CS.Pyoel (Ad35-PyCS).

| Immunization schedule | Viral vector-prime | Viral vector-boost (after 8 weeks) | # mice | ELISPOT/ serum | challenge |
|---|---|---|---|---|---|
| Prime-boost/ challenge | Ad5-PyCS | Ad5-PyCS | 12 | 2 wks post boost (6 mice) | 2 wks post boost (6 mice) |
| Prime-boost/ challenge | Ad35-PyCS | Ad35-PyCS | 12 | 2 wks post boost (6 mice) | 2 wks post boost (6 mice) |
| Prime-boost/ challenge | Ad5-PyCS | Ad35-PyCS | 12 | 2 wks post boost (6 mice) | 2 wks post boost (6 mice) |
| Prime-boost/ challenge | Ad35-PyCS | Ad5-PyCS | 12 | 2 wks post boost (6 mice) | 2 wks post boost (6 mice) |
| Prime-boost/ challenge | Ad5- empty | Ad35- empty | 12 | 2 wks post boost (6 mice) | 2 wks post boost (6 mice) |

TABLE VII

Immunization, challenge and read-out schedules for mice in a prime-boost vaccination set-up using Ad5.CS.Pfalc (Ad5-PfCS) and Ad35.CS.Pfalc (Ad35-PfCS), with or without GPI anchor.

| Immunization schedule | Viral vector-prime | Viral vector-boost (after 8 weeks) | # mice | ELISPOT/ serum | ELISPOT/ serum |
|---|---|---|---|---|---|
| Prime-boost/ challenge | Ad5-PfCS | Ad5-PfCS | 12 | 2 wks post boost (6 mice) | 6/10/16 wks post boost (6 mice) |
| Prime-boost/ challenge | Ad35-PfCS | Ad35-PfCS | 12 | 2 wks post boost (6 mice) | 2 wks post boost (6 mice) |
| Prime-boost/ challenge | Ad5-PfCS | Ad35-PfCS | 12 | 2 wks post boost (6 mice) | 2 wks post boost (6 mice) |
| Prime-boost/ challenge | Ad35-PfCS | Ad5-PfCS | 12 | 2 wks post boost (6 mice) | 2 wks post boost (6 mice) |
| Prime-boost/ challenge | Ad5-empty | Ad35-empty | 12 | 2 wks post boost (6 mice) | 2 wks post boost (6 mice) |

REFERENCES (the contents of each of which, and the contents of every other publication, including patent publications such as PCT International Patent Publications referenced in this application, being incorporated herein by this reference)

Bruña-Romero O., G. González-Aseguinolaza, J. C. R. Hafalla, et al. (2001a) Complete, long-lasting protection against malaria of mice primed and boosted with two distinct viral vectors expressing the same plasmodial antigen. *Proc. Natl. Acad. Sci. U.S.A.* 98:11491-11496.

Bruña-Romero O., J. C. R. Hafalla, G. González-Aseguinolaza, G. Sano, M. Tsjui and F. Zavala (2001b) Detection of malaria liver stages in mice infected through the bite of a single *Anopheles* mosquito using a highly sensitive real-time PCR. *Int. J. Parasitol.* 31:1499-1502.

Clyde D. F., H. Most, V. C. McCarthy and J.P. Vanderberg (1973) Immunization of men against sporozoite-induced falciparum malaria. *Am. J. Med. Sci.* 266:169-177.

De Jong J. C., A. G. Wermenbol, M. W. Verweij-Uijterwaal, K. W. Slaterus, P. Wertheim-Van Dillen, G. J. Van Doornum, S. H. Khoo and J. C. Hierholzer (1999) Adenoviruses from human immunodeficiency virus-infected individuals, including two strains that represent new candidate serotypes Ad50 and Ad51 of species B1 and D, respectively. *J. Clin. Microbiol.* 37:3940-3945.

Gandon S., M. J. Mackinnon, S. Nee and A. F. Read (2001) Imperfect vaccines and the evolution of pathogen virulence. *Nature* 414:751-756.

Gilbert S. C., J. Schneider, C. M. Hannan, et al. (2002) Enhanced CD8 T-cell immunogenicity and protective efficacy in a mouse malaria model using a recombinant adenoviral vaccine in heterologous prime-boost immunisation regimes. *Vaccine* 20:1039-1045.

Gordon D. M., T. W. McGovern, U. Krzych, J. C. Cohen, I. Schneider, R. LaChance, D. G. Heppner, G. Yuan, M. Hollingdale, M. Slaoui, et al. (1995) Safety, immunogenicity, and efficacy of a recombinantly produced *Plasmodium falciparum* circumsporozoite protein-hepatitis B surface antigen subunit vaccine. *J. Infect. Dis.* 171:1576-1585.

Kurtis J. D., M. R. Hollingdale, A. J. F. Luty, D. E. Lanar, U. Krzych and P. E. Duffy (2001) Pre-erythrocytic immunity to *Plasmodium falciparum*: the case for an LSA-1 vaccine. *Trends in Parasitology* 17:219-223.

Lockyer M. J., K. Marsh and C. I. Newbold (1989) Wild isolates of *Plasmodium falciparum* show extensive polymorphism in T-cell epitopes of the circumsporozoite protein. *Mol. Biochem. Parasitol.* 37:275-280.

Moran P. and I. W. Caras (1994) Requirements for glycosylphosphatidylinositol attachment are similar but not identical in mammalian cells and parasitic protozoa. *J. Cell. Biol.* 125:333-343.

Nardin E. H., J. M. Calvo-Calle, G. A. Oliveira, et al. (2001) A totally synthetic polyoxime malaria vaccine containing *Plasmodium falciparum* B cell and universal T-cell epitopes elicits immune responses in volunteers of diverse HLA types. *J. Immunol.* 166:481-489.

Narum D. L., S. Kumar, W. O. Rogers, et al. (2001) Codon optimization of gene fragments encoding *Plasmodium falciparum* merzoite proteins enhances DNA vaccine protein expression and immunogenicity in mice. *Infect. and Immun.* 69:7250-7253.

Nussenzweig R. S., J. Vanderberg, H. Most and C. Orton (1967) Protective immunity produced by the injection of X-irradiated sporozoites of *Plasmodium berghei*. *Nature* 216:160-162.

Romero P., J. L. Maryanski, G. Corradin, et al. (1989) Cloned cytotoxic T-cells recognize an epitope in the circumsporozoite protein and protect against malaria. *Nature* 341:323-326.

Rodrigues E. G., F. Zavala, D. Eichinger, et al. (1997) Single immunizing dose of recombinant adenovirus efficiently induces CD8+ T-cell-mediated protective immunity against malaria. *J. Immunol.* 158:1268-1274.

Scheiblhofer S., D. Chen, R. Weiss, et al. (2001) Removal of the circumsporozoite protein (CSP) glycosylphosphatidylinositol signal sequence from a CSP DNA vaccine enhances induction of CSP-specific Th2-type immune responses and improves protection against malaria infection. *Eur. J. Immunol.* 31:692-698.

Zevering Y., C. Khamboonruang and M. F. Good (1994) Effect of polymorphism of sporozoite antigens on T-cell activation. *Res. Immunol.* 145:469-476.

What is claimed is:

1. A method for generating an immune response against a *Plasmodium falciparum* circumsporozoite (CS) antigen in a subject, the method comprising: a) administering to the subject a composition comprising a replication-defective adenovirus comprising a nucleic acid molecule encoding the protein of SEQ ID NO: 6, wherein the nucleic acid molecule is codon-optimized; and b) further administering to the subject a composition comprising RTS,S.

2. The method according to claim 1, wherein the nucleic acid molecule used in step a) is codon optimized for elevated expression in a mammal.

3. The method according to claim 2, wherein the mammal is a human.

4. The method according to claim 1, wherein the nucleic acid molecule used in step a) comprises SEQ ID NO:4.

5. The method according to claim 1, wherein the subject is a mammal.

6. The method according to claim 5, wherein the mammal is a human.

7. The method according to claim 1, further comprising:

c) administering to the subject a second composition comprising a recombinant replication-defective adenovirus comprising a nucleic acid molecule encoding the protein of SEQ ID NO:6, wherein the nucleic acid molecule is codon-optimized.

8. The method according to claim 7, wherein the adenovirus in each composition is of a different serotype.

9. The method according to claim 1, wherein the replication-defective adenovirus is from a serotype selected from the group consisting of Ad11, Ad26, Ad34, Ad35, Ad48, Ad49, and Ad50.

10. The method according to claim 9, wherein the replication-defective adenovirus is from Ad35.

11. The method according to claim 1, wherein step b) is performed after step a).

12. The method according to claim 1, wherein step b) is performed before step a).

13. The method according to claim 7, wherein step c) is performed after step a) and before step b).

14. The method according to claim 7, wherein step c) is performed after step a) and wherein step a) is performed after step b).

15. The method according to claim 7, wherein step c) is performed after step b) and wherein step b) is performed after step a).

* * * * *

SEQUENCE LISTING

```
<160> NUMBER OF SEQ ID NOS: 19

<210> SEQ ID NO 1
<211> LENGTH: 1193
<212> TYPE: DNA
<213> ORGANISM: Artificial
<220> FEATURE:
<223> OTHER INFORMATION: Description of Artificial Sequence: Codon-
      optimised circumsporozoite gene of Plasmodium falciparum, clone
      02-148
<220> FEATURE:
<221> NAME/KEY: CDS
<222> L

```
                                                                           627
Asn Pro Asn Val Asp Pro Asn Ala Asn Pro Asn Ala Asn Pro Asn Ala
190                 195                 200                 205 aat ccc aac gct aac ccg aac gca aac cct aac gcc aat ccg aat gcc            675
Asn Pro Asn Ala Asn Pro Asn Ala Asn Pro Asn Ala Asn Pro Asn Ala
                210                 215                 220 aac cca aac gcc aac ccg aac gct aat ccg aat gct aac ccg aat gct            723
Asn Pro Asn Ala Asn Pro Asn Ala Asn Pro Asn Ala Asn Pro Asn Ala
            225                 230                 235 aat cct aac gca aac cca aat gca aac ccc aat gca aac ccg aac gcc            771
Asn Pro Asn Ala Asn Pro Asn Ala Asn Pro Asn Ala Asn Pro Asn Ala
        240                 245                 250 aat ccc aac gcc aat cct aat gcc aac aag aac aat cag ggc aac ggc            819
Asn Pro Asn Ala Asn Pro Asn Ala Asn Lys Asn Asn Gln Gly Asn Gly
    255                 260                 265 cag ggc cac aac atg ccc aac gac ccc aac cgg aac gtg gac gag aac            867
Gln Gly His Asn Met Pro Asn Asp Pro Asn Arg Asn Val Asp Glu Asn
270                 275                 280                 285 gcc aac gcc aac aac gcc gtg aag aac aac aac gag gag ccc agc                915
Ala Asn Ala Asn Asn Ala Val Lys Asn Asn Asn Glu Glu Pro Ser
                290                 295                 300 gac aag cac atc gag cag tac ctg aag aag atc cag aac agc ctg agc            963
Asp Lys His Ile Glu Gln Tyr Leu Lys Lys Ile Gln Asn Ser Leu Ser
                305                 310                 315 acc gag tgg agc ccc tgc agc gtg acc tgc ggc aac ggc att cag gtg            1011
Thr Glu Trp Ser Pro Cys Ser Val Thr Cys Gly Asn Gly Ile Gln Val
            320                 325                 330 cgg atc aag ccc ggc agc gcc aac aag ccc aag gac gag ctg gac tac            1059
Arg Ile Lys Pro Gly Ser Ala Asn Lys Pro Lys Asp Glu Leu Asp Tyr
        335                 340                 345 gag aat gac atc gag aag aag atc tgc aag atg gag aag tgc agc agc            1107
Glu Asn Asp Ile Glu Lys Lys Ile Cys Lys Met Glu Lys Cys Ser Ser
350                 355                 360                 365 gtg ttc aac gtg gtg aac agc gcc atc ggc ctg att atg gtg ctg agc            1155
Val Phe Asn Val Val Asn Ser Ala Ile Gly Leu Ile Met Val Leu Ser
                370                 375                 380 ttc ctg ttc ctg aac tgaagatctg ctgataagga tcc                              1193
Phe Leu Phe Leu Asn
            385

<210> SEQ ID NO 2
<211> LENGTH: 386
<212> TYPE: PRT
<213> ORGANISM: Artificial
<220> FEATURE:
<223> OTHER INFORMATION: Description of Artificial Sequence: Codon-
      optimised circumsporozoite gene of Plasmodium falciparum, clone
      02-148

<400> SEQUENCE: 2

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
```

```
            65                  70                  75                  80
Asn Asn Gly Asp Asn Gly Arg Glu Gly Lys Asp Glu Asp Lys Arg Asp
                        85                  90                  95
Gly Asn Asn Glu Asp Asn Glu Lys Leu Arg Lys Pro Lys His Lys Lys
            100                 105                 110
Leu Lys Gln Pro Ala Asp Gly Asn Pro Asp Pro Asn Ala Asn Pro Asn
            115                 120                 125
Val Asp Pro Asn Ala Asn Pro Asn Val Asp Pro Asn Ala Asn Pro Asn
        130                 135                 140
Val Asp Pro Asn Ala Asn Pro Asn Ala Asn Pro Asn Ala Asn Pro Asn
145                 150                 155                 160
Ala Asn Pro Asn Ala Asn Pro Asn Ala Asn Pro Asn Ala Asn Pro Asn
                165                 170                 175
Ala Asn Pro Asn Ala Asn Pro Asn Ala Asn Pro Asn Ala Asn Pro Asn
                180                 185                 190
Val Asp Pro Asn Ala Asn Pro Asn Ala Asn Pro Asn Ala Asn Pro Asn
            195                 200                 205
Ala Asn Pro Asn Ala Asn Pro Asn Ala Asn Pro Asn Ala Asn Pro Asn
        210                 215                 220
Ala Asn Pro Asn Ala Asn Pro Asn Ala Asn Pro Asn Ala Asn Pro Asn
225                 230                 235                 240
Ala Asn Pro Asn Ala Asn Pro Asn Ala Asn Pro Asn Ala Asn Pro Asn
                245                 250                 255
Ala Asn Pro Asn Ala Asn Lys Asn Asn Gln Gly Asn Gly Gln Gly His
                260                 265                 270
Asn Met Pro Asn Asp Pro Asn Arg Asn Val Asp Glu Asn Ala Asn Ala
            275                 280                 285
Asn Asn Ala Val Lys Asn Asn Asn Asn Glu Glu Pro Ser Asp Lys His
        290                 295                 300
Ile Glu Gln Tyr Leu Lys Lys Ile Gln Asn Ser Leu Ser Thr Glu Trp
305                 310                 315                 320
Ser Pro Cys Ser Val Thr Cys Gly Asn Gly Ile Gln Val Arg Ile Lys
                325                 330                 335
Pro Gly Ser Ala Asn Lys Pro Lys Asp Glu Leu Asp Tyr Glu Asn Asp
            340                 345                 350
Ile Glu Lys Lys Ile Cys Lys Met Glu Lys Cys Ser Ser Val Phe Asn
        355                 360                 365
Val Val Asn Ser Ala Ile Gly Leu Ile Met Val Leu Ser Phe Leu Phe
    370                 375                 380
Leu Asn
385

<210> SEQ ID NO 3
<211> LENGTH: 386
<212> TYPE: PRT
<213> ORGANISM: Plasmodium falciparum
<220> FEATURE:
<221> NAME/KEY: SIGNAL
<222> LOCATION: (1)..(30)
<223> OTHER INFORMATION: Signal peptide region
<220> FEATURE:
<221> NAME/KEY: REPEAT
<222> LOCATION: (124)..(259)
<223> OTHER INFORMATION: Region of 4 NVDP and in total 30 NAVP repeats
<220> FEATURE:
<221> NAME/KEY: LIPID
<222> LOCATION: (359)..(386)
<223> OTHER INFORMATION: GPI-ANCHOR
<220> FEATURE:
```

```
<221> NAME/KEY: MUTAGEN
<222> LOCATION: (373)..(373)
<223> OTHER INFORMATION: Ser to Ala substitution, elimination of
      glycosylation site

<400> SEQUENCE: 3
```

Met Met Arg Lys Leu Ala Ile Leu Ser Val Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
                100                 105                 110

Leu Lys Gln Pro Ala Asp Gly Asn Pro Asp Pro Asn Ala Asn Pro Asn
            115                 120                 125

Val Asp Pro Asn Ala Asn Pro Asn Val Asp Pro Asn Ala Asn Pro Asn
130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Val Asp Pro Asn Ala Asn Pro Asn Ala Asn Pro Asn Ala Asn Pro Asn
            195                 200                 205

Ala Asn Pro Asn Ala Asn Pro Asn Ala Asn Pro Asn Ala Asn Pro Asn
            210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Lys Asn Asn Gln Gly Asn Gly Gln Gly His
            260                 265                 270

Asn Met Pro Asn Asp Pro Asn Arg Asn Val Asp Glu Asn Ala Asn Ala
            275                 280                 285

Asn Asn Ala Val Lys Asn Asn Asn Glu Glu Pro Ser Asp Lys His
        290                 295                 300

Ile Glu Gln Tyr Leu Lys Lys Ile Gln Asn Ser Leu Ser Thr Glu Trp
305                 310                 315                 320

Ser Pro Cys Ser Val Thr Cys Gly Asn Gly Ile Gln Val Arg Ile Lys
            325                 330                 335

Pro Gly Ser Ala Asn Lys Pro Lys Asp Glu Leu Asp Tyr Glu Asn Asp
            340                 345                 350

Ile Glu Lys Lys Ile Cys Lys Met Glu Lys Cys Ser Ser Val Phe Asn
            355                 360                 365

Val Val Asn Ser Ala Ile Gly Leu Ile Met Val Leu Ser Phe Leu Phe
            370                 375                 380

Leu Asn

<210> SEQ ID NO 4
<211> LENGTH: 1154
<212> TYPE: DNA
<213> ORGANISM: Artificial
<220> FEATURE:
<223> OTHER INFORMATION: Description of Artificial Sequence: Codon-
      optimised circumsporozoite gene of Plasmodium falciparum strain
      3D7, clone 02-659
<220> FEATURE:
<221> NAME/KEY: CDS
<222> LOCATION: (13)..(1128)
<223> OTHER INFORMATION: Nucleic acid sequence encoding translated
      protein
<220> FEATURE:
<221> NAME/KEY: sig_peptide
<222> LOCATION: (13)..(102)
<223> OTHER INFORMATION: Nucleic acid sequence encoding signal sequence
      of translated protein

<400> SEQUENCE: 4

```
aagcttgcca cc atg atg agg aaa ctg gcc atc ctg agc gtg agc agc ttc      51
              Met Met Arg Lys Leu Ala Ile Leu Ser Val Ser Ser Phe
               1               5                  10 ctg ttc gtg gag gcc ctg ttt cag gag tac cag tgc tac ggc agc agc        99
Leu Phe Val Glu Ala Leu Phe Gln Glu Tyr Gln Cys Tyr Gly Ser Ser
        15                  20                  25 agc aac acc cgg gtg ctg aac gag ctg aac tac gac aac gcc ggc acc       147
Ser Asn Thr Arg Val Leu Asn Glu Leu Asn Tyr Asp Asn Ala Gly Thr
 30                  35                  40                  45 aac ctg tac aac gag ctg gag atg aac tac tac ggc aag cag gag aac       195
Asn Leu Tyr Asn Glu Leu Glu Met Asn Tyr Tyr Gly Lys Gln Glu Asn
                 50                  55                  60 tgg tac agc ctg aag aag aac agc cgg tct ctg ggc gag aac gac gac       243
Trp Tyr Ser Leu Lys Lys Asn Ser Arg Ser Leu Gly Glu Asn Asp Asp
             65                  70                  75 ggc aac aac aac aac ggc gac aac ggc cgg gag ggc aag gac gag gac       291
Gly Asn Asn Asn Asn Gly Asp Asn Gly Arg Glu Gly Lys Asp Glu Asp
         80                  85                  90 aag cgg gac ggc aac aac gag gac aac gag aag ctg cgg aag ccc aag       339
Lys Arg Asp Gly Asn Asn Glu Asp Asn Glu Lys Leu Arg Lys Pro Lys
     95                 100                 105 cac aag aaa ctt aag cag ccc gcc gac ggc aac ccc gac ccc aac gcc       387
His Lys Lys Leu Lys Gln Pro Ala Asp Gly Asn Pro Asp Pro Asn Ala
110                 115                 120                 125 aac ccc aac gtg gac ccc aac gcc aat cct aat gtc gac ccc aat gcc       435
Asn Pro Asn Val Asp Pro Asn Ala Asn Pro Asn Val Asp Pro Asn Ala
                130                 135                 140 aat ccg aac gtt gat ccc aat gcg aat cct aac gct aac ccc aat gcc       483
Asn Pro Asn Val Asp Pro Asn Ala Asn Pro Asn Ala Asn Pro Asn Ala
            145                 150                 155 aac cca aat gcc aat cca aat gca aat ccc aac gcc aat cca aac gca       531
Asn Pro Asn Ala Asn Pro Asn Ala Asn Pro Asn Ala Asn Pro Asn Ala
        160                 165                 170 aac cct aat gct aat cca aac gct aat cct aat gcc aat ccc aat gct       579
Asn Pro Asn Ala Asn Pro Asn Ala Asn Pro Asn Ala Asn Pro Asn Ala
    175                 180                 185 aac cca aac gtc gat cct aac gca aat ccg aac gct aac ccc aac gca       627
Asn Pro Asn Val Asp Pro Asn Ala Asn Pro Asn Ala Asn Pro Asn Ala
190                 195                 200                 205 aat ccc aac gct aac ccg aac gca aac cct aac gcc aat ccg aat gcc       675
Asn Pro Asn Ala Asn Pro Asn Ala Asn Pro Asn Ala Asn Pro Asn Ala
                210                 215                 220
```

```
aac cca aac gcc aac ccg aac gct aat ccg aat gct aac ccg aat gct    723
Asn Pro Asn Ala Asn Pro Asn Ala Asn Pro Asn Ala Asn Pro Asn Ala
            225                 230                 235 aat cct aac gca aac cca aat gca aac ccc aat gca aac ccg aac gcc    771
Asn Pro Asn Ala Asn Pro Asn Ala Asn Pro Asn Ala Asn Pro Asn Ala
    240                 245                 250 aat ccc aac gcc aat cct aat gcc aac aag aac aat cag ggc aac ggc    819
Asn Pro Asn Ala Asn Pro Asn Ala Asn Lys Asn Asn Gln Gly Asn Gly
255                 260                 265 cag ggc cac aac atg ccc aac gac ccc aac cgg aac gtg gac gag aac    867
Gln Gly His Asn Met Pro Asn Asp Pro Asn Arg Asn Val Asp Glu Asn
270                 275                 280                 285 gcc aac gcc aac agc gcc gtg aag aac aac aac aac gag gag ccc agc    915
Ala Asn Ala Asn Ser Ala Val Lys Asn Asn Asn Asn Glu Glu Pro Ser
            290                 295                 300 gac aag cac atc aag gag tac ctg aac aag atc cag aac agc ctg agc    963
Asp Lys His Ile Lys Glu Tyr Leu Asn Lys Ile Gln Asn Ser Leu Ser
    305                 310                 315 acc gag tgg agc ccc tgc agc gtg acc tgc ggc aac ggc att cag gtg   1011
Thr Glu Trp Ser Pro Cys Ser Val Thr Cys Gly Asn Gly Ile Gln Val
320                 325                 330 cgg atc aag ccc ggc agc gcc aac aag ccc aag gac gag ctg gac tac   1059
Arg Ile Lys Pro Gly Ser Ala Asn Lys Pro Lys Asp Glu Leu Asp Tyr
        335                 340                 345 gcc aat gac atc gag aag aag atc tgc aag atg gag aag tgc agc agc   1107
Ala Asn Asp Ile Glu Lys Lys Ile Cys Lys Met Glu Lys Cys Ser Ser
350                 355                 360                 365 gtg ttc aac gtg gtg aac tcc tgataaagat ctgctgataa ggatcc          1154
Val Phe Asn Val Val Asn Ser
                370

<210> SEQ ID NO 5
<211> LENGTH: 372
<212> TYPE: PRT
<213> ORGANISM: Artificial
<220> FEATURE:
<223> OTHER INFORMATION: Description of Artificial Sequence: Codon-
      optimised circumsporozoite gene of Plasmodium falciparum strain
      3D7, clone 02-659

<400> SEQUENCE: 5

Met Met Arg Lys Leu Ala Ile Leu Ser Val Ser Ser Ph

```
            145                 150                 155                 160
Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
                180                 185                 190

Val Asp Pro Asn Ala Asn Pro Asn Ala Asn Pro Asn Ala Asn Pro Asn
                195                 200                 205

Ala Asn Pro Asn Ala Asn Pro Asn Ala Asn Pro Asn Ala Asn Pro Asn
                210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Lys Asn Asn Gln Gly Asn Gly Gln Gly His
                260                 265                 270

Asn Met Pro Asn Asp Pro Asn Arg Asn Val Asp Glu Asn Ala Asn Ala
                275                 280                 285

Asn Ser Ala Val Lys Asn Asn Asn Glu Glu Pro Ser Asp Lys His
            290                 295                 300

Ile Lys Glu Tyr Leu Asn Lys Ile Gln Asn Ser Leu Ser Thr Glu Trp
305                 310                 315                 320

Ser Pro Cys Ser Val Thr Cys Gly Asn Gly Ile Gln Val Arg Ile Lys
                325                 330                 335

Pro Gly Ser Ala Asn Lys Pro Lys Asp Glu Leu Asp Tyr Ala Asn Asp
                340                 345                 350

Ile Glu Lys Lys Ile Cys Lys Met Glu Lys Cys Ser Ser Val Phe Asn
                355                 360                 365

Val Val Asn Ser
            370

<210> SEQ ID NO 6
<211> LENGTH: 372
<212> TYPE: PRT
<213> ORGANISM: Plasmodium falciparum
<220> FEATURE:
<221> NAME/KEY: SIGNAL
<222> LOCATION: (1)..(30)
<223> OTHER INFORMATION: Signal sequence region
<220> FEATURE:
<221> NAME/KEY: REPEAT
<222> LOCATION: (124)..(259)
<223> OTHER INFORMATION: Region of 4 NVDP and in total 30 NAVP repeats
<220> FEATURE:
<221> NAME/KEY: LIPID
<222> LOCATION: (359)..(372)
<223> OTHER INFORMATION: GPI-ANCHOR

<400> SEQUENCE: 6

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
        50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
```

85                  90                  95
Gly Asn Asn Glu Asp Asn Glu Lys Leu Arg Lys Pro Lys His Lys Lys
            100                 105                 110

Leu Lys Gln Pro Ala Asp Gly Asn Pro Asp Pro Asn Ala Asn Pro Asn
            115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
            165                 170                 175

Ala Asn Pro Asn Ala Asn Pro Asn Ala Asn Pro Asn Ala Asn Pro Asn
            180                 185                 190

Val Asp Pro Asn Ala Asn Pro Asn Ala Asn Pro Asn Ala Asn Pro Asn
            195                 200                 205

Ala Asn Pro Asn Ala Asn Pro Asn Ala Asn Pro Asn Ala Asn Pro Asn
            210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
            245                 250                 255

Ala Asn Pro Asn Ala Asn Lys Asn Asn Gln Gly Asn Gly Gln Gly His
            260                 265                 270

Asn Met Pro Asn Asp Pro Asn Arg Asn Val Asp Glu Asn Ala Asn Ala
            275                 280                 285

Asn Ser Ala Val Lys Asn Asn Asn Asn Glu Glu Pro Ser Asp Lys His
            290                 295                 300

Ile Lys Glu Tyr Leu Asn Lys Ile Gln Asn Ser Leu Ser Thr Glu Trp
305                 310                 315                 320

Ser Pro Cys Ser Val Thr Cys Gly Asn Gly Ile Gln Val Arg Ile Lys
            325                 330                 335

Pro Gly Ser Ala Asn Lys Pro Lys Asp Glu Leu Asp Tyr Ala Asn Asp
            340                 345                 350

Ile Glu Lys Lys Ile Cys Lys Met Glu Lys Cys Ser Ser Val Phe Asn
            355                 360                 365

Val Val Asn Ser
    370

<210> SEQ ID NO 7
<211> LENGTH: 1115
<212> TYPE: DNA
<213> ORGANISM: Artificial
<220> FEATURE:
<223> OTHER INFORMATION: Description of Artificial Sequence: Codon-
      optimised cirrcumsporozoite gene of Plasmodium yoelii, clone
      02-149
<220> FEATURE:
<221> NAME/KEY: CDS
<222> LOCATION: (17)..(1084)
<223> OTHER INFORMATION: Nucleic acid sequence encoding translated
      protein
<220> FEATURE:
<221> NAME/KEY: sig_peptide
<222> LOCATION: (17)..(73)
<223> OTHER INFORMATION: Nucleic acid sequence encoding signal sequence
      of translated protein

<400> SEQUENCE: 7
aagcttgcta gccacc atg aag aag tgc acc atc ctg gtg gtg gcc agc ctg      52
                Met Lys Lys Cys Thr Ile Leu Val Val Ala Ser Leu -continued

```
         1               5                    10
ctg ctg gtg gac agc ctg ctg ccc ggc tac ggc cag aac aag agc gtg    100
Leu Leu Val Asp Ser Leu Leu Pro Gly Tyr Gly Gln Asn Lys Ser Val
         15                  20                  25 cag gcc cag cgg aac ctg aac gag ctg tgc tac aac gag gag aac gac    148
Gln Ala Gln Arg Asn Leu Asn Glu Leu Cys Tyr Asn Glu Glu Asn Asp
         30                  35                  40 aac aag ctg tac cac gtg ctg aac agc aag aac ggc aag att tac aac    196
Asn Lys Leu Tyr His Val Leu Asn Ser Lys Asn Gly Lys Ile Tyr Asn
45                  50                  55                  60 cgg aac atc gtg aac cgg ctg ctg ggc gac gcc ctg aac ggc aag ccc    244
Arg Asn Ile Val Asn Arg Leu Leu Gly Asp Ala Leu Asn Gly Lys Pro
              65                  70                  75 gag gag aag aag gac gac ccc ccc aag gac ggc aac aag gac gac ctg    292
Glu Glu Lys Lys Asp Asp Pro Pro Lys Asp Gly Asn Lys Asp Asp Leu
              80                  85                  90 ccc aag gag gag aag aaa gac gat ctg cct aag gag gaa aaa aag gac    340
Pro Lys Glu Glu Lys Lys Asp Asp Leu Pro Lys Glu Glu Lys Lys Asp
              95                 100                 105 gat cct cct aag gac ccc aag aag gac gat cct ccc aaa gag gcc cag    388
Asp Pro Pro Lys Asp Pro Lys Lys Asp Asp Pro Pro Lys Glu Ala Gln
         110                 115                 120 aac aag ctg aac cag ccc gtg gtg gcc gac gag aac gtg gac cag ggc    436
Asn Lys Leu Asn Gln Pro Val Val Ala Asp Glu Asn Val Asp Gln Gly
125                 130                 135                 140 cct ggc gcc cct cag ggc ccc ggg gcc cct cag ggc cct gga gcc cct    484
Pro Gly Ala Pro Gln Gly Pro Gly Ala Pro Gln Gly Pro Gly Ala Pro
                  145                 150                 155 caa gga ccc gga gcc ccc cag gga cct ggc gct cct cag gga ccc ggc    532
Gln Gly Pro Gly Ala Pro Gln Gly Pro Gly Ala Pro Gln Gly Pro Gly
              160                 165                 170 gct cca cag ggc cca ggg gcc ccc cag ggc cca ggg gca ccc cag ggc    580
Ala Pro Gln Gly Pro Gly Ala Pro Gln Gly Pro Gly Ala Pro Gln Gly
         175                 180                 185 cca ggc gcc cca caa ggt ccc ggg gct cct cag ggt ccc gga gca cct    628
Pro Gly Ala Pro Gln Gly Pro Gly Ala Pro Gln Gly Pro Gly Ala Pro
         190                 195                 200 cag ggg cct gga gca cca cag ggg cct ggg gcc cca caa ggg cca ggc    676
Gln Gly Pro Gly Ala Pro Gln Gly Pro Gly Ala Pro Gln Gly Pro Gly
205                 210                 215                 220 gct ccc caa ggg cct ggc gca ccc cag gag ccc ccc cag cag ccc cct    724
Ala Pro Gln Gly Pro Gly Ala Pro Gln Glu Pro Pro Gln Gln Pro Pro
                  225                 230                 235 cag cag ccc ccc cag caa cct ccc caa cag cct ccc cag caa cca cca    772
Gln Gln Pro Pro Gln Gln Pro Pro Gln Gln Pro Pro Gln Gln Pro Pro
              240                 245                 250 cag cag cca cca cag caa ccc agg ccc cag ccc gac ggc aac aac aac    820
Gln Gln Pro Pro Gln Gln Pro Arg Pro Gln Pro Asp Gly Asn Asn Asn
         255                 260                 265 aac aat aac aac aac ggc aac aac aac gag gac agc tac gtg ccc agc    868
Asn Asn Asn Asn Asn Gly Asn Asn Asn Glu Asp Ser Tyr Val Pro Ser
         270                 275                 280 gcc gag cag atc ctg gag ttc gtg aag cag atc agc agc caa ctg acc    916
Ala Glu Gln Ile Leu Glu Phe Val Lys Gln Ile Ser Ser Gln Leu Thr
285                 290                 295                 300 gag gag tgg agc cag tgc agc gtg acc tgc ggc agc ggc gtg cgg gtg    964
Glu Glu Trp Ser Gln Cys Ser Val Thr Cys Gly Ser Gly Val Arg Val
                  305                 310                 315 cgg aag cgg aag aac gtg aac aag cag ccc gag aac ctg acc ctg gag   1012
Arg Lys Arg Lys Asn Val Asn Lys Gln Pro Glu Asn Leu Thr Leu Glu
```

```
                320                 325                 330
gac atc gac acc gag atc tgc aag atg gac aag tgc agc agc atc ttc      1060
Asp Ile Asp Thr Glu Ile Cys Lys Met Asp Lys Cys Ser Ser Ile Phe
        335                 340                 345 aac atc gtg agc aac agc ctg ggc tgaagatctg ctgataagtt taaacggatc     1114
Asn Ile Val Ser Asn Ser Leu Gly
    350                 355 c                                                                    1115
```

<210> SEQ ID NO 8
<211> LENGTH: 356
<212> TYPE: PRT
<213> ORGANISM: Artificial
<220> FEATURE:
<223> OTHER INFORMATION: Description of Artificial Sequence: Codon-optimised cirrcumsporozoite gene of Plasmodium yoelii, clone 02-149

<400> SEQUENCE: 8

```
Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Gln Pro Pro Gln Gln Pro Pro
225                 230                 235                 240

Gln Gln Pro Pro Gln Pro Gln Gln Pro Pro Gln Gln Pro Pro Gln Pro
                245                 250                 255

Gln Gln Pro Arg Pro Gln Pro Asp Gly Asn Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300
```

```
Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu Gly
        355

<210> SEQ ID NO 9
<211> LENGTH: 356
<212> TYPE: PRT
<213> ORGANISM: Plasmodium yoelii
<220> FEATURE:
<221> NAME/KEY: SIGNAL
<222> LOCATION: (1)..(19)
<223> OTHER INFORMATION: Signal sequence region
<220> FEATURE:
<221> NAME/KEY: REPEAT
<222> LOCATION: (138)..(225)
<223> OTHER INFORMATION: Region of 15 QGPGAP repeats
<220> FEATURE:
<221> NAME/KEY: REPEAT
<222> LOCATION: (229)..(254)
<223> OTHER INFORMATION: Region of 7 PQQP repeats

<400> SEQUENCE: 9

Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
                20                  25                  30

Asn Leu Asn Glu Leu Cys Tyr Asn Glu Glu Asn Asp Asn Lys Leu Tyr
            35                  40                  45

His Val Leu Asn Ser Lys Asn Gly Lys Ile Tyr Asn Arg Asn Ile Val
        50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Leu Pro Lys Glu Glu
                85                  90                  95

Lys Lys Asp Asp Leu Pro Lys Glu Glu Lys Lys Asp Asp Pro Pro Lys
                100                 105                 110

Asp Pro Lys Lys Asp Asp Pro Pro Lys Glu Ala Gln Asn Lys Leu Asn
            115                 120                 125

Gln Pro Val Val Ala Asp Glu Asn Val Asp Gln Gly Pro Gly Ala Pro
        130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Pro Pro Gln Gln Pro Pro
225                 230                 235                 240

Gln Gln Pro Pro Gln Gln Pro Pro Gln Gln Pro Pro Gln Gln Pro Pro
                245                 250                 255
```

```
Gln Gln Pro Arg Pro Gln Pro Asp Gly Asn Asn Asn Asn Asn Asn
        260                 265                 270

Asn Gly Asn Asn Asn Glu Asp Ser Tyr Val Pro Ser Ala Glu Gln Ile
    275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu Gly
        355

<210> SEQ ID NO 10
<211> LENGTH: 4
<212> TYPE: PRT
<213> ORGANISM: Plasmodium falciparum

<400> SEQUENCE: 10

Asn Ala Asn Pro
1

<210> SEQ ID NO 11
<211> LENGTH: 4
<212> TYPE: PRT
<213> ORGANISM: Plasmodium falciparum

<400> SEQUENCE: 11

Asn Val Asp Pro
1

<210> SEQ ID NO 12
<211> LENGTH: 11
<212> TYPE: PRT
<213> ORGANISM: Plasmodium falciparum

<400> SEQUENCE: 12

Glu Asn Ala Asn Ala Asn Asn Ala Val Lys Asn
1               5                   10

<210> SEQ ID NO 13
<211> LENGTH: 23
<212> TYPE: DNA
<213> ORGANISM: Artificial
<220> FEATURE:
<223> OTHER INFORMATION: Description of Artificial Sequence:
      oligonucleotide Forw.Falc

<400> SEQUENCE: 13
ccaagcttgc caccatgatg agg                                          23

<210> SEQ ID NO 14
<211> LENGTH: 27
<212> TYPE: DNA
<213> ORGANISM: Artificial
<220> FEATURE:
<223> OTHER INFORMATION: Description of Artificial Sequence:
      oligonucleotide Rev.Falc.CS-28

<400> SEQUENCE: 14
ccggatcctc agcagatctt cttctcg                                      27
```

```
<210> SEQ ID NO 15
<211> LENGTH: 27
<212> TYPE: DNA
<213> ORGANISM: Artificial
<220> FEATURE:
<223> OTHER INFORMATION: Description of Artificial Sequence:
      oligonucleotide Rev.Falc.CS-14

<400> SEQUENCE: 15
ccggatcctc agctgttcac cacgttg                                          27

<210> SEQ ID NO 16
<211> LENGTH: 22
<212> TYPE: DNA
<213> ORGANISM: Artificial
<220> FEATURE:
<223> OTHER INFORMATION: Description of Artificial Sequence:
      oligonucleotide SV40for

<400> SEQUENCE: 16
caatgtatct tatcatgtct ag                                               22

<210> SEQ ID NO 17
<211> LENGTH: 35
<212> TYPE: DNA
<213> ORGANISM: Artificial
<220> FEATURE:
<223> OTHER INFORMATION: Description of Artificial Sequence:
      oligonucleotide pIXRmfe

<400> SEQUENCE: 17
ctctctcaat tgcagataca aaactacata agacc                                 35

<210> SEQ ID NO 18
<211> LENGTH: 32
<212> TYPE: DNA
<213> ORGANISM: Artificial
<220> FEATURE:
<223> OTHER INFORMATION: Description of Artificial Sequence:
      oligonucleotide pIX35mfe

<400> SEQUENCE: 18
ctctctcaat tgtctgtctt gcagctgtca tg                                    32

<210> SEQ ID NO 19
<211> LENGTH: 18
<212> TYPE: PRT
<213> ORGANISM: Plasmodium yoelii

<400> SEQUENCE: 19

Gln Gly Pro Gly Ala Pro Gln Gly Pro Gly Ala Pro Gln Gly Pro Gly
1               5                   10                  15

Ala Pro
```